(12) United States Patent
Mandel

(10) Patent No.: US 11,062,797 B2
(45) Date of Patent: Jul. 13, 2021

(54) METHOD AND SYSTEM FOR OBTAINING AND USING PHARMACOKINETIC DATA IN DRUG ADMINISTRATION

(71) Applicant: Continuous Precision Medicine, Raleigh, NC (US)

(72) Inventor: Jeff E. Mandel, Media, PA (US)

(73) Assignee: Continuous Precision Medicine, Raleigh, NC (US)

(*) Notice: Subject to any disclaimer, the term of this patent is extended or adjusted under 35 U.S.C. 154(b) by 809 days.

(21) Appl. No.: 14/880,816

(22) Filed: Oct. 12, 2015

(65) Prior Publication Data

US 2016/0103977 A1 Apr. 14, 2016

Related U.S. Application Data

(60) Provisional application No. 62/062,525, filed on Oct. 10, 2014.

(51) Int. Cl.
*G16H 20/17* (2018.01)
*A61M 5/14* (2006.01)

(52) U.S. Cl.
CPC .......... *G16H 20/17* (2018.01); *A61M 5/14* (2013.01); *A61M 2205/50* (2013.01); *A61M 2205/502* (2013.01)

(58) Field of Classification Search
CPC ...... G06Q 50/22; G06Q 50/24; G06F 19/322; G06F 19/323–327; G16H 20/00;
(Continued)

(56) References Cited

U.S. PATENT DOCUMENTS

2005/0246416 A1* 11/2005 Blomquist .............. H04L 67/12
709/203
2006/0149705 A1* 7/2006 Friedlander ............ G16H 50/70
(Continued)

FOREIGN PATENT DOCUMENTS

WO WO-2005072792 A1 * 8/2005 .......... A61M 5/1723

OTHER PUBLICATIONS

Mandel et al.—"The Variability of Response to Propofol Is Reduced When A Clinical Observation Is Incorporated In The Control: A Simulation Study", Anesthesia & Analgesia, Jun. 2012, vol. 114, No. 6, pp. 1221-1229.*
(Continued)

*Primary Examiner* — Jason S Tiedeman
(74) *Attorney, Agent, or Firm* — Oblon, McClelland, Maier & Neustadt, L.L.P.

(57) ABSTRACT

There is provided a method for dosing a drug to a patient, including (a) administering the drug to the patient according to a titration dosing schedule, where the titration dosing schedule is determined from a database storing data containing observations of previous patient responses to the drug, and the titration dosing schedule is associated with a subcohort of a cohort of patients, where a subcohort classification is based on one or more factors associated with variability of the drug; (b) monitoring the patient during the administering (a) to determine when a desired clinical endpoint is reached; (c) administering the drug to the patient according to a maintenance dosing schedule, where the maintenance dosing schedule is based on an estimate of drug level, where the estimate is based on (i) when the desired clinical endpoint is reached, and (ii) a pharmacokinetic model for the subcohort; and (d) updating the database to incorporate data from the monitoring (b) of the patient.

17 Claims, 19 Drawing Sheets

(58) Field of Classification Search
CPC ........ G16H 20/10; G16H 20/17; G16H 40/00; G16H 40/60; G16H 40/63; G16H 40/67; A61M 5/14; A61M 2205/50; A61M 2205/502
USPC ........................................................ 705/2, 3
See application file for complete search history.

(56) References Cited

U.S. PATENT DOCUMENTS

| | | | | |
|---|---|---|---|---|
| 2009/0221532 A1* | 9/2009 | Gibiansky | ............... | A61P 25/08 514/130 |
| 2010/0212666 A1* | 8/2010 | Bouillon | ............... | A61M 5/142 128/203.14 |
| 2013/0253362 A1* | 9/2013 | Scheib | ................. | A61B 5/4821 600/544 |
| 2014/0379629 A1* | 12/2014 | Loew-Baselli | ....... | G06F 19/704 706/52 |
| 2015/0100294 A1* | 4/2015 | Wilson | ................... | G16H 50/50 703/11 |
| 2015/0127372 A1* | 5/2015 | Berry | .................. | G06F 19/3456 705/2 |

OTHER PUBLICATIONS

Cortinez et al.—"Influence of obesity on propofol pharmacokinetics: derivation of a pharmacokinetic model", British Journal of Anaesthesia 105 (4), pp. 448-456 (2010).

Johnson et al.—"An Evaluation of Remifentanil Propofol Response Surfaces for Loss of Responsiveness, Loss of Response to Surrogates of Painful Stimuli and Laryngoscopy in Patients Undergoing Elective Surgery", Anesthesia & Analgesia, vol. 106, No. 2, Feb. 2008, pp. 471-479.

De Vito et al.—"Drug-induced sleep endoscopy: conventional versus target controlled infusion techniques—a randomized controlled study", Eur Arch Otorhinolaryngol, 2010.

* cited by examiner

METHOD AND SYSTEM FOR OBTAINING AND USING PHARMACOKINETIC DATA IN DRUG ADMINISTRATION

CROSS-REFERENCE TO RELATED APPLICATIONS

This application claims the benefit of priority under 35 U.S.C. § 119(e) to U.S. Provisional Application No. 62/062,525, filed on Oct. 10, 2014, the entirety of which is incorporated herein by reference.

FIELD

This application relates generally to the field of pharmacology and drug administration. In particular, disclosed embodiments relate to systems and methods for using clinical observations and pharmacological models in clinical care. More specifically, these systems and methods are used for dosing a drug administered to a patient.

BACKGROUND

For most drugs, proper dosing is complicated by several factors. First, the time course of drug levels over time varies from patient to patient. This is termed pharmacokinetic uncertainty. Second, the drug level that corresponds to a desired clinical effect varies from patient to patient. This is termed pharmacodynamic uncertainty. Clinicians "titrate to effect," but without insight into the pharmacokinetics, the dosing may result in peaks that occur too rapidly to accurately estimate the concentration at which the clinical effect occurred, or may take an inordinately long time to achieve the desired clinical effect. Additionally, pharmacokinetic and pharmacodynamics models are generally derived from a small number of subjects, while thousands of patients receive these medications every day. The insight gained from a single patient encounter at best adds to the expertise of a single clinician, rather than contributing to the corpus of knowledge on the response of all patients to the drug. This leads clinicians to believe that drug administration is not amenable to improvement through information science.

SUMMARY

Consistent with disclosed embodiments, an improved system and method is provided for effectively overcoming the aforementioned difficulties in drug administration.

Consistent with an embodiment, there is provided a method for dosing a drug to a patient, the method comprising: (a) administering the drug to the patient according to a titration dosing schedule, wherein the titration dosing schedule is determined from a database storing data comprising observations of previous patient responses to the drug, and the titration dosing schedule is associated with a subcohort of patients, wherein a subcohort classification is based on one or more factors associated with variability of the drug; (b) monitoring the patient during the administering (a) to determine when a desired clinical endpoint is reached; (c) administering the drug to the patient according to a maintenance dosing schedule, wherein the maintenance dosing schedule is based on an estimate of a drug level, wherein the estimate is based on (i) when the desired clinical endpoint was reached in the monitoring (b), and (ii) a pharmacokinetic model for the subcohort; and (d) updating the database to incorporate data from the monitoring (b) of the patient.

Consistent with an embodiment, there is provided a system for dosing a drug to a patient, the system comprising circuitry configured to: (a) administer the drug to the patient according to a titration dosing schedule, wherein the titration dosing schedule is determined from a database storing data comprising observations of previous patient responses to the drug, and the titration dosing schedule is associated with a subcohort of a cohort of patients, wherein a subcohort classification is based on one or more factors associated with variability of the drug; (b) monitor the patient during (a) to determine when a desired clinical endpoint is reached; (c) administer the drug to the patient according to a maintenance dosing schedule, wherein the maintenance dosing schedule is based on an estimate of a drug level, wherein the estimate is based on (i) when the desired clinical endpoint was reached in (b), and (ii) a pharmacokinetic model for said subcohort; and (d) update the database to incorporate patient data from (b).

Consistent with an embodiment, there is provided a nontransitory computer-readable storage medium having computer executable instructions stored thereon, which when executed by a processor, causes the processor to perform a method for dosing a drug to a patient, the method comprising: (a) administering said drug to said patient according to a titration dosing schedule, wherein the titration dosing schedule is determined from a database storing data comprising observations of previous patient responses to the drug, and the titration dosing schedule is associated with a subcohort of a cohort of patients, wherein a subcohort classification is based on one or more factors associated with variability of said drug; (b) monitoring the patient during the administering (a) to determine when a desired clinical endpoint is reached; (c) administering said drug to said patient according to a maintenance dosing schedule, wherein the maintenance dosing schedule is based on an estimate of a drug level, wherein the estimate is based on (i) when the desired clinical endpoint was reached in the monitoring (b), and (ii) a pharmacokinetic model for said subcohort; and (d) updating the database to incorporate data from the monitoring (b) of said patient.

Consistent with an embodiment, there is provided a method for determining a dosing of a drug to a new patient, comprising:
   obtaining observations of at least one previous patient response to the drug generated by administering the drug to the previous patient according to a titration dosing schedule, wherein the titration dosing schedule is determined from a database storing data comprising observations of the at least one previous patient response to the drug, and the titration dosing schedule is associated with a subcohort of a cohort of patients, wherein a subcohort classification is based on one or more factors associated with variability of the drug, monitoring the previous patient during the administering to determine when a desired clinical endpoint is reached, administering the drug to the previous patient according to a maintenance dosing schedule, wherein the maintenance dosing schedule is based on an estimate of a drug level, wherein the estimate is based on (i) when the desired clinical endpoint was reached in the monitoring, and (ii) a pharmacokinetic model for the subcohort, and updating the database to incorporate data from the monitoring of the previous patient; and
   calculating, using processing circuitry and using data from the database storing data comprising the observations of the at least one previous patient responses to the drug, an update to the titration dosing schedule for the new patient.

Other features and advantages will become apparent from the following detailed description examples and figures. It should be understood, however, that the detailed description and the specific examples, while indicating preferred embodiments, are given by way of illustration only, since various changes and modifications will become apparent to those skilled in the art from this detailed description.

DETAILED DESCRIPTION

In the following description, various exemplary embodiments are described. For purposes of explanation, specific configurations and details are set forth in order to provide a thorough understanding of the embodiments. However, it will also be apparent to one skilled in the art that the embodiments may be practiced without the specific details presented herein. Furthermore, well known features may be omitted or simplified in order not to obscure the embodiments.

Unless specifically stated otherwise, as apparent from the following discussions, it is appreciated that throughout the specification discussions utilizing terms such as "processing," "computing," "calculating," "determining," or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices.

Figure 1A:
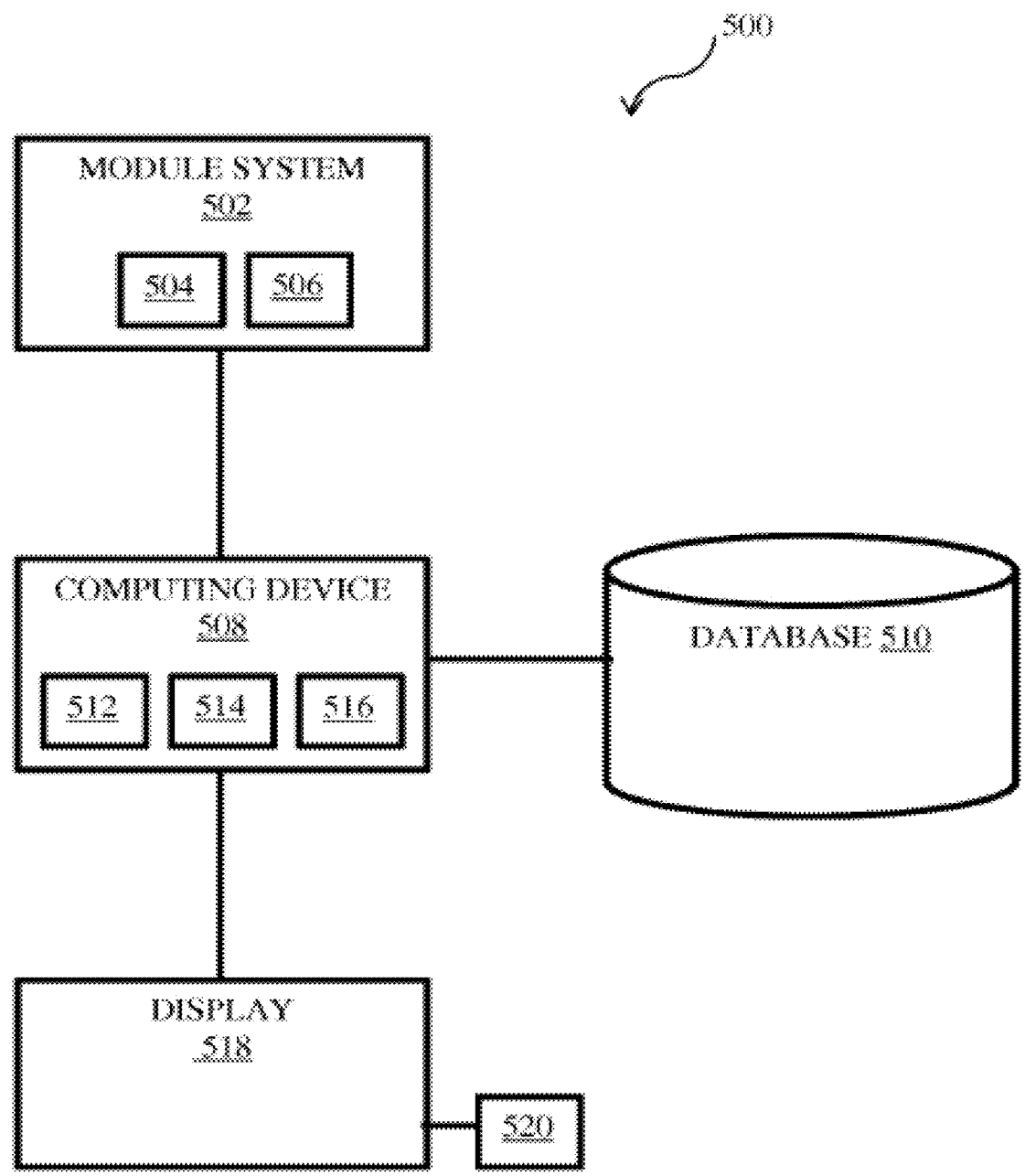
FIGS. 1A and 1B are exemplary schematic diagrams illustrating systems for dosing a drug to a patient, according to disclosed embodiments.
Figure 1B:
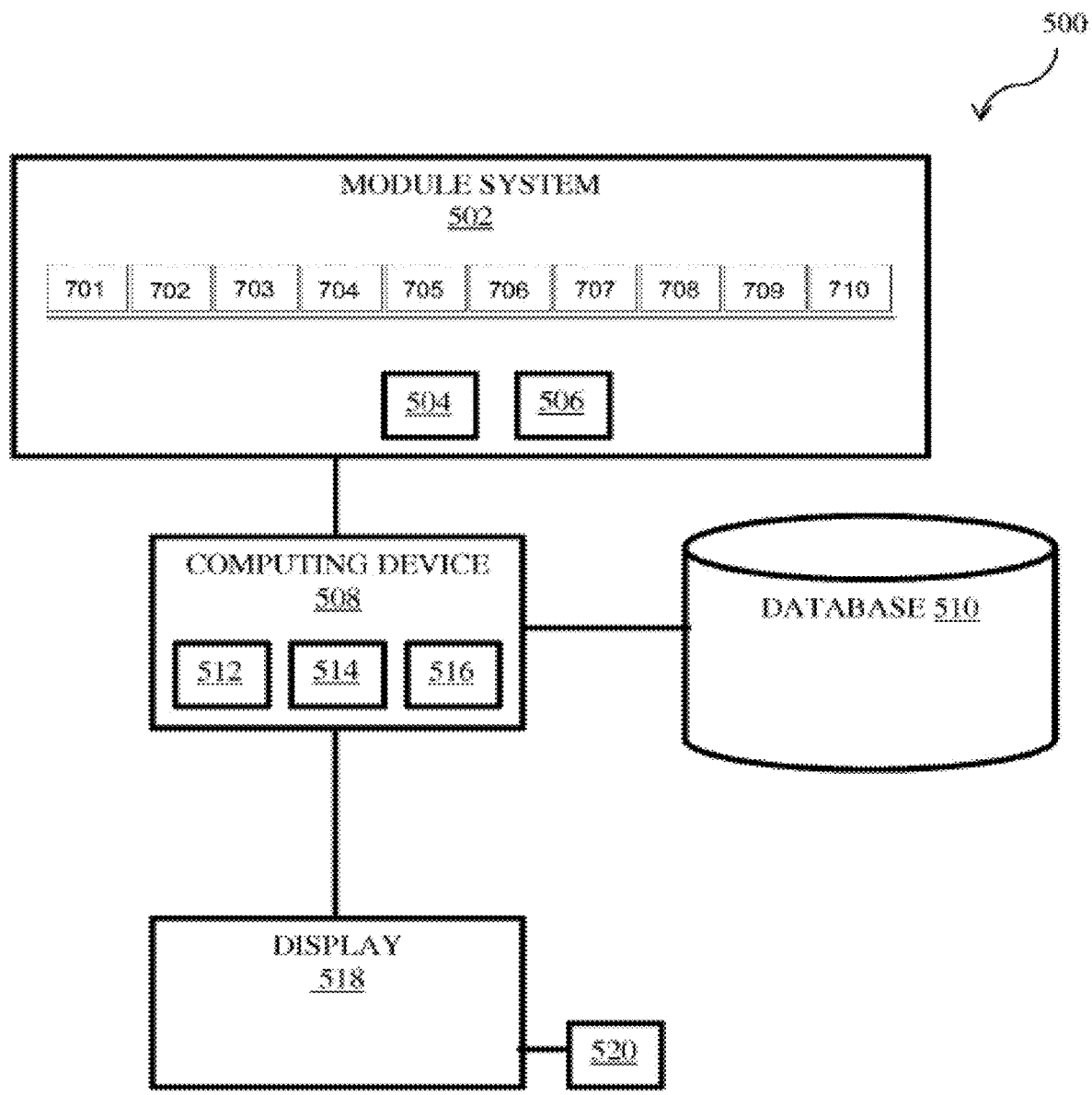

FIGS. 1A and 1B schematically illustrate examples of a system for dosing a drug to a patient. Although the FIGS. 1A and 1B show an exemplary conventional general-purpose digital environment, it will be understood that other computing environments may also be used. For example, one or more embodiments may use an environment having fewer than or otherwise more than all of the various aspects shown in FIGS. 1A and 1B, and these aspects may appear in various combinations and sub-combinations that will be apparent to one of ordinary skill in the art.

As shown in FIGS. 1A and 1B, system 500 may include a computing device 508. Computing device 508 may include, for example, any suitable processing system, computing system, computing device, processing device, computer, processor, or the like, and may be implemented using any suitable combination of hardware and/or software. Computing device 508 may include for example one or more processor(s) 512, memory 514 and software 516. Data may be transferred, for example, to computing device 508. The data may be stored in the memory 514 as for example digital information and transferred to computing device 508 by uploading, copying or transmitting the digital information. Processor 504 may communicate with computing device 508 via wired or wireless command and execution signals.

In some embodiments using a matching method, computing device 508 may include units, modules, means, and circuitry for various steps described herein for dosing a drug to a patient.

Memory 506 and 514 and database 510 may include cache memory, long term memory such as a hard drive, and/or external memory, for example, including random access memory (RAM), read only memory (ROM), dynamic RAM (DRAM), synchronous DRAM (SD-RAM), flash memory, volatile memory, non-volatile memory, cache memory, buffer, short term memory unit, long term memory unit, or other suitable memory units or storage units. Memory 506 and 514 and database 510 may store instructions (e.g., software 516) and data to execute embodiments of the aforementioned methods, steps and functionality (e.g., in long term memory, such as a hard drive).

Computing device 508 may include a computing module having machine-executable instructions. The instructions may include, for example, a data processing mechanism (including, for example, embodiments of methods described herein) and a modeling mechanism. These instructions may be used to cause processor 512 using associated software 516 modules programmed with the instructions to perform the operations described. Alternatively, the operations may be performed by specific hardware that may contain hardwired logic for performing the operations, or by any combination of programmed computer components and custom hardware components.

Embodiments may include an article such as a computer or processor readable medium, or a computer or processor storage medium, such as, for example, a memory, a nontransitory computer-readable storage medium, such as a disk drive or a USB flash memory, encoding, including or storing instructions, e.g., computer-executable instructions, which when executed by a processor or controller, carry out methods disclosed herein.

In exemplary embodiments, a user (e.g., clinician) has a user computer with Internet access that is operatively coupled to a server via a network, which can be an internet or intranet. User computer and server may implement various aspects of the embodiments that are apparent in the detailed description. For example, a user computer may be in the form of a personal computer, a tablet personal computer or a personal digital assistant (PDA). The user computer may be configured with an application program that communicates with the server. This application program can include a conventional browser or browser-like programs.

Processor 512 may perform various methods described herein. For example, processor 512 may execute the method of FIG. 2.

Figure 3:
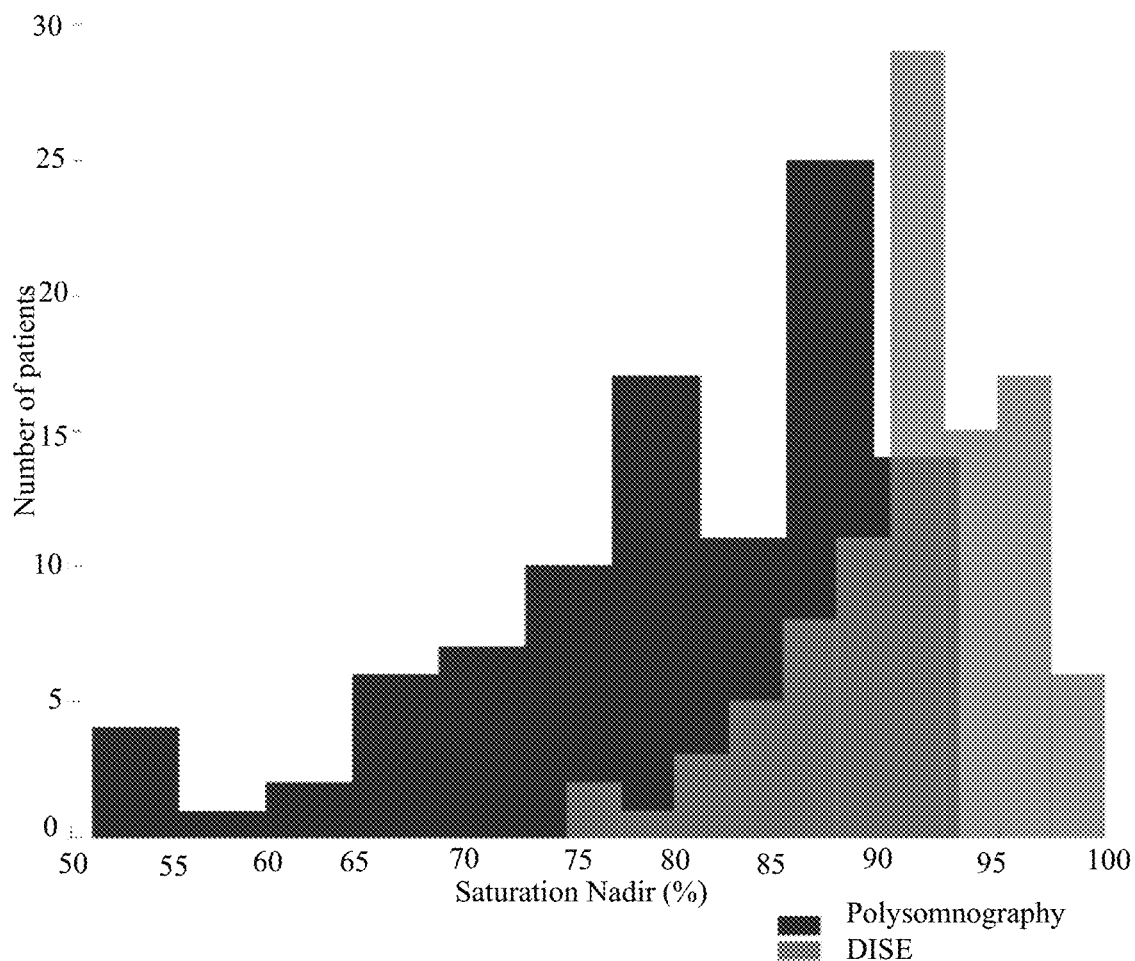
FIG. 3 is an exemplary histogram showing nadir oxygen saturation during polysomnography and drug induced sleep endoscopy.

Display 518 may display results and/or intermediate data such as outcomes, probabilities, virtual progeny phenomes, for example, as shown in the diagram of FIG. 3. Display 518 may include a monitor or screen, such as an organic light emitting diode (LED) screen, liquid crystal display (LCD) screen, thin film transistor display, or the like. In one embodiment, the user may interact with display 518 using input device(s) 520.

Input device(s) 520 may include a keyboard, pointing device (e.g., mouse, trackball, pen,), a touch screen or cursor direction keys, communicating information and command selections to processor 514. Input device 520 may communicate user direction information and command selections to the processor 514. For example, a user may use input device 520 to select.

Processor 504 and 514, which can be components of a module system 502, may include, for example, one or more processors, controllers, central processing units ("CPUs"), or graphical processing units ("GPUs"), or field programmable gate arrays ("FPGAs"). Software 516 may be stored, for example, in memory 514.

As shown in FIG. 1B, system 500 can be comprised of module system 502, which may include a plurality of modules or units capable of performing operations described herein. In an embodiment, module system 502 may include an assigning module 701, a receiving module 702, an administration module 703, a monitoring module 704, an estimating module 705, a maintenance module 706, a dose administration module 707, an updating module 708, a determining module 709, and a storage module 710.

Assigning module 701 may assign a patient to a subcohort of a cohort of patients based on one or more factors associated with drug variability. In general, a subcohort is a subset of patients of a cohort. Receiving module 702 may receive from database 510 of dosing schedules a titration dosing schedule associated with the subcohort for the patient. The titration dosing schedule may be determined from a database storing data comprising observations of previous patient responses to the drug. Administration module 703 may facilitate administering the drug to the patient according to the titration dosing schedule. Monitoring module 704 may facilitate monitoring the patient during the administration to determine when a desired clinical endpoint is reached. In exemplary embodiments, the desired clinical endpoint may be sedation, visible airway collapse, airway obstruction, or loss of genioglossus tone. Estimating module 705 may estimate a drug level and maintenance module 706 may receive a maintenance dosing schedule to maintain that drug level based on the determination of the endpoint and a pharmacokinetic model for the subcohort. A dose administration module 707 may administer the drug to the patient according to the maintenance dosing schedule. Updating module 708 may update database 510 to incorporate the patient's data. Determining module 709 may determine how much the database is improved by the patient's data. The storage module may store and archive the data for future use.

Figure 2:
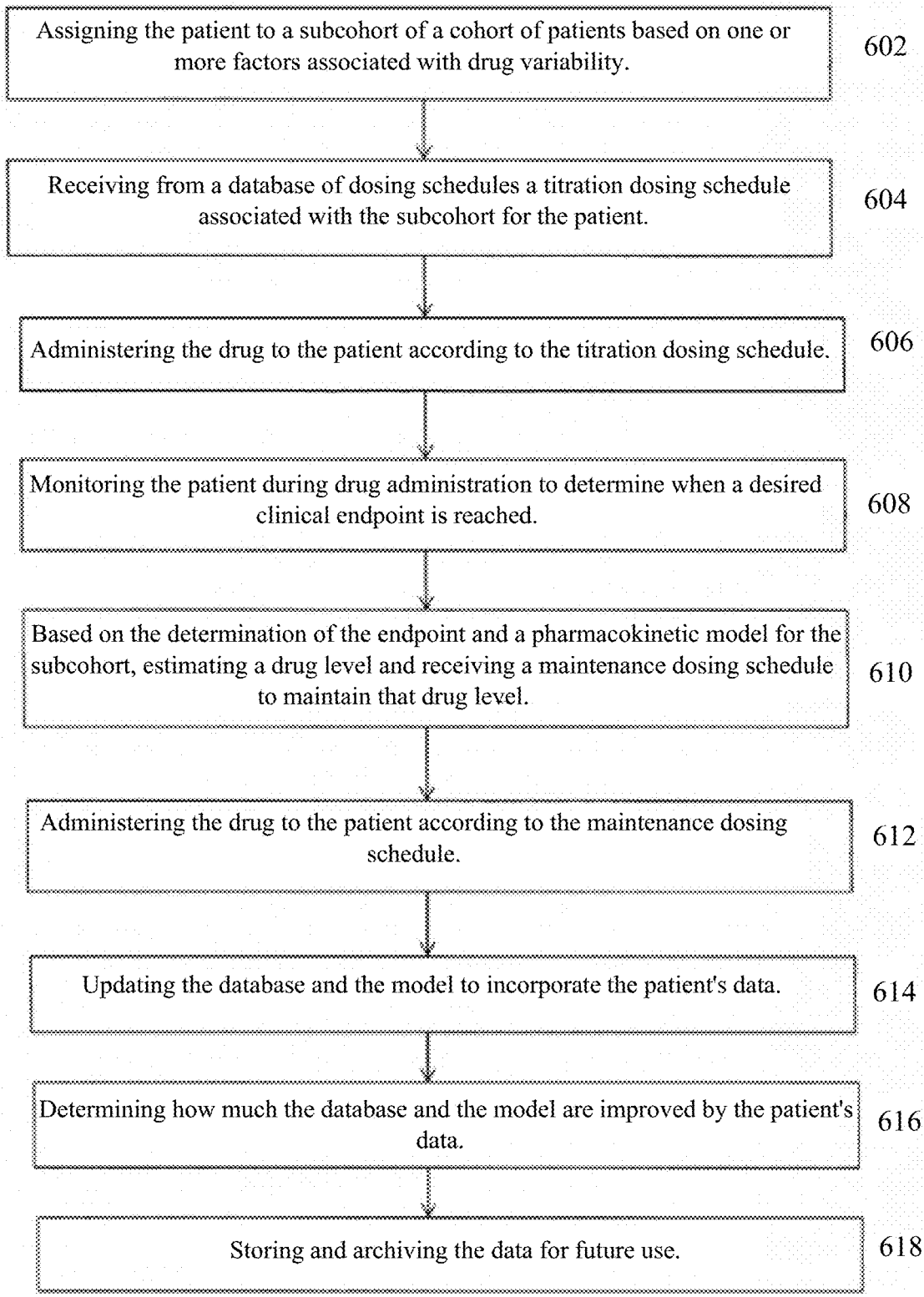
FIG. 2 is an exemplary flowchart illustrating a method for dosing a drug to a patient, according to an embodiment.

FIG. 2 illustrates a method for dosing a drug to a patient, according to an embodiment. The term "drug," as used herein, may refer to any drug that can be administered to a patient. In an embodiment, the route of administration of the drug is intravenous infusion. In another embodiment, the route is oral administration, for example ingestion of a pill or capsule. In embodiments, the drug may be an anesthetic, for example propofol, an analgesic, an antidepressant, an anxiolytic agent, or an antibiotic. In embodiments, administration of the drug leads to a clinical effect that is observed as a distinct transition in time due to the drug reaching an effective level.

As shown in FIG. 2, item 602, an assigning module or unit (e.g., 701) may assign the patient to a subcohort of a cohort of patients based on one or more factors associated with drug variability. Examples of factors may include, but are not limited to, factors selected from age, weight, gender, race and ethnicity of the patient.

As shown in item 604, a receiving module or unit (e.g., 702) may receive from database 510 of dosing schedules a titration dosing schedule associated with said subcohort for the patient. The titration dosing schedule may be determined from a database storing data comprising observations of previous patient responses to the drug. As shown in item 606, an administration module or unit (e.g., 703) may facilitate administering the drug to the patient according to the titration dosing schedule. In one embodiment, the titration schedule includes proceeding from a lowest level of drug at which any previous patient has ever responded to a highest level of drug ever required to reach the desired clinical endpoint, over a defined interval of time. In a particular embodiment, the probability of achieving a clinical endpoint increases linearly over the interval of time.

The observations of previous patient responses to the drug may include observations of at least one previous patient response to the drug. The previous patient response to the drug may be generated by administering the drug to the previous patient according to a titration dosing schedule, wherein the titration dosing schedule is determined from a database storing data comprising observations of the at least one previous patient response to the drug, and the titration dosing schedule is associated with a subcohort of a cohort of patients, wherein a subcohort classification is based on one or more factors associated with variability of the drug, monitoring the previous patient during the administering to determine when a desired clinical endpoint is reached, administering the drug to the previous patient according to a maintenance dosing schedule, wherein the maintenance dosing schedule is based on an estimate of a drug level, wherein the estimate is based on (i) when the desired clinical endpoint was reached in the monitoring, and (ii) a pharmacokinetic model for the subcohort, and updating the database to incorporate data from the monitoring of the previous patient.

The observation of previous patient responses may be used to update a titration dosing schedule for a new patient. The update to the titration dosing schedule may be calculated using processing circuitry and using data from a database storing data comprising observations of one or more previous patient responses to the drug. The drug may be administered to the new patient using the updated titration dosing schedule.

As shown in item 608, a monitoring module or unit (e.g., 704) may facilitate monitoring the patient during the administration to determine when a desired clinical endpoint is reached. The monitoring step may be performed by a clinician or an automated monitor. The term "clinical endpoint," as used herein, may refer to a desired clinical trait or a phenotypic trait. In a particular embodiment, the clinical endpoint is a desired level of sedation.

As shown in item 610, based on the determination of the endpoint and a pharmacokinetic model for said subcohort, an estimating module or unit (e.g., 705) may estimate a drug level and a maintenance module or unit (e.g., 706) may receive a maintenance dosing schedule to maintain that drug level. As shown in item 612, an administering module or unit (e.g., 707) may administer the drug to the patient according to the maintenance dosing schedule. As shown in item 614, system 500 may include one or more features (e.g., 708) that may update the database and the model to incorporate said patient's data. The updating of the model may comprise minimizing a difference between a probability density function for the subcohort and the entire cohort of patients.

As shown in item 616, system 500 may include one or more features (e.g., 709) that may determine how much the database is improved by said patient's data. As shown in item 618, system 500 may include one or more features (e.g., 710) that may store and archive the data for future use.

In an embodiment, system 500 may be configured to perform the operations described herein in a real-time. In another embodiment, system 500 is capable of performing the calculations and other operations in real-time.

In an embodiment, the drug administration may be performed by any suitable delivery device or method known to one of skill in the art. In one aspect, the drug described herein may be administered using a pump or other drug delivery device. In one embodiment, the pump or other drug delivery device is manually controlled by a user. In another embodiment, the pump or other drug delivery device is automatically controlled by a processor that receives the dosing schedules.

The process described herein may be performed using a user interface configured to be able to receive the factors and to record the clinical endpoint from a user. The user interface may be configured to provide the titration and maintenance dosing schedules to the user. The user interface may be configured to transmit the titration and maintenance dosing schedules to a controller unit that controls the administration of the drug.

In an embodiment, the user interface may comprise a screen, such as an organic light emitting diode screen, liquid crystal display screen, thin film transistor display, and the like. The graphical user interface may generate a wide range of colors, or for example, a black and white screen may be used.

In certain embodiments, the graphical user interface may be touch-sensitive, and it may use any technology known to skilled artisans including, but not limited to, resistive, surface acoustic wave, capacitive, infrared, strain gauge, optical imaging, dispersive signal technology, acoustic pulse recognition, frustrated total internal reflection, and diffused laser imaging.

The systems described herein may also include an operating system that runs on the processor, including, for example, UNIX® and WINDOWS®, each of which may be configured to run many tasks at the same time, e.g., a multitasking operating systems. In an embodiment, the methods are utilized with a wireless communication and/or computation device, such as a mobile phone, personal digital assistant, personal computer, and the like. Moreover, the computing system may be operable to wirelessly transmit data to wireless or wired communication devices using a data network, such as the Internet, or a local area network (LAN), wide-area network (WAN), cellular network, or other wireless networks known to those skilled in the art.

The systems and methods disclosed herein are further illustrated by the following examples. The examples are not to be construed as limiting the scope or content of the application in any way.

Example 1

Probability Ramp Propofol Infusion for Sleep Endoscopy

Drug induced sleep endoscopy (DISE) employs sedative-hypnotics to induce moderate obstruction to facilitate anatomic differentiation of obstructive physiology. The epidemic of obstructive sleep apnea (OSA) coupled with a substantial continuous positive airway pressure (CPAP) failure rate and new surgical approaches have promoted the use of DISE as a diagnostic tool. Palatal collapse at the velopharynx, lateral collapse of the pharyngeal walls, and obstruction at the tongue base are common sites of dynamic obstruction. In contrast to other diagnostic approaches, real-time visual observation of the airway during DISE can differentiate the relative role of each mechanism in a given patient. DISE may also provide prognostic information regarding therapeutic interventions such as mandibular advancement devices.

Obstruction commonly, but not always, occurs contemporaneously with loss of consciousness. Induction with propofol to loss of consciousness is readily accomplished; however, reliable prediction of the necessary propofol dose to achieve and maintain obstruction without causing prolonged loss of consciousness or oxygen desaturation is challenging. Manual bolus approaches require an experienced practitioner to obtain consistent results. Overshoots can invoke clinically concerning oxygen desaturation and aborted procedures while under dosing may add substantial time to the procedure and discomfort to the patient. Target-controlled infusion (TCI) may reduce the variability of propofol titration but TCI is not approved for clinical use in North America. Moreover, titration by TCI requires small serial increments in the target to achieve the desired clinical endpoint, a time-consuming process that is not well suited to high-volume throughput or patient comfort. Manual and TCI approaches assume that the anesthetist can surmise the appropriate target level for a given patient. Previous work has demonstrated in simulation a method for producing a continuously increasing probability of loss of consciousness with a simple sequence of infusion rates (Mandel & Sarraf, *Anesth Analg.* 2012; 114:1221-9). The inventor, however, hypothesized that such an approach, with a hybrid pharmacokinetic/pharmacodynamic model, would permit reliable and efficient titration of propofol to an endpoint of visible airway collapse and/or loss of genioglossus tone in a population with severe OSA. The inventor further hypothesized that the risk of oxygen desaturation during DISE would be no worse than that observed during sleep studies.

Ninety-seven (97) patients were enrolled in a prospective study of transoral robotic resection of the tongue base; the examples described below provided a secondary outcome measure of that study. All patients had previously undergone an overnight polysomnography study in a sleep laboratory and had attempted continuous positive airway pressure (CPAP) as a therapeutic approach, but found this not to be helpful. The apnea-hypopnea index (AHI) for each patient was recorded from the sleep study. For each patient the saturation nadirs from the sleep study and DISE were paired for statistical analysis. All patients were screened with drug induced sleep endoscopy with propofol infusions determined by custom software written in MATLAB®, which has been previously described. The system utilizes the Cortinez pharmacokinetic model (Cortinez et al., *Br J Anaesth.* 2010; 105:448-56.) and the Johnson pharmacodynamic model (Johnson et al., *Anesth Analg.* 2008; 106:471-9.) to determine an infusion sequence comprised of a bolus, initial infusion, secondary infusion, and a time for transition from the initial to secondary infusion using the age and weight of the individual patient. This sequence minimizes the difference between the predicted probability of loss of responsiveness and a linear ramp. This is termed probability ramp control (PRC). A brief description of the mathematical approach can be found below. The MATLAB® program (an embodiment of the system) performed the calculations, indicated the time to perform the transition to the second infusion, and logged the time at which obstruction was noted. Patient characteristics are presented in Table 1.

TABLE 1

Demographics of analyzed patients (n = 97)

| | |
|---|---|
| Age (y) (Mean ± SD) | 48.8 ± 9.0 years |
| Gender | F 14 M 83 |
| Height (Mean ± SD) | 1.77 ± 0.91 m |
| Weight (Mean ± SD) | 102.6 ± 19.5 kg |
| BMI (Median (IQR)) | 32.1 (6.8) kg/m$^2$ |
| AHI (Median (IQR)) | 48 (32) |
| Sleep Study SaO$_2$ Nadir (Median (IQR)) | 81.0 (11.2) % |

All DISE studies were performed in an operating room with standard monitors and resuscitation equipment. A single otorhinolaryngologist performed each nasopharyngoscopy. Propofol was administered by an anesthesiologist. No topical anesthesia was employed, and no intravenous drugs other than propofol were used. All DISE patients received 2 liters per minute supplemental oxygen via a nasal cannula placed in the mouth. Supplemental oxygen was not used during polysomnography studies (as is typical for this procedure). Pulse oximetry data was recorded for subsequent analysis from a Nellcor pulse oximeter (Covidien, Mansfield, Mass.) at 30-second intervals by the DocuSys anesthesia record keeping system. Sedation was provided with propofol infused through a pigtail side-port adapter with a free-flowing intravenous catheter. A 60 mL Becton-Dickinson syringe was loaded with 40 mL of propofol and the line primed until propofol was visibly present at the hub. A Baxter AS50 pump (Baxter, Deerfield, Ill.) was programmed with the initial bolus and infusion rates as determined by the control system. Following this initial bolus of propofol, an Olympus model BF-3C160 pediatric bronchoscope (Olympus Corporation, Center Valley, Pa.) was passed via the naris. With the bronchoscope in position to observe the velopharynx, the sedation sequence proceeded until the onset of obstruction was noted. This was identified as the obstruction clinical endpoint. Observation of the pharynx was performed for a sufficient period to obtain images of the anatomic site(s) of obstruction. The infusion was then terminated and the patient allowed to recover. Patient characteristics and derived pharmacokinetic measures were assessed for normal distribution using the Lilliefors test at 5% significance level using the Statistics Toolbox of MATLAB® 8.0 (MathWorks, Natick, Mass.). Saturation nadirs were assessed with the Lilliefors test, which rejected the hypothesis that they were normally distributed. Comparison of saturation nadirs from DISE and polysomnography was performed with both the paired and unpaired Student's t-test. Correlation of DISE saturation nadir and body mass index (BMI), apnea-hypopnea index (AHI), propofol effect-site concentration at obstruction, and age were assessed by Spearman's rho, with Fisher's transformation applied to determine 95% confidence intervals. No power analysis was performed for this study, as it was a secondary outcome measure for the larger study of transoral robotic surgery.

The subject population was characterized by a median BMI of 32.1 (±6.8) and median AHI of 48 (±32) The median time to obstruction, as determined by the otorhinolaryngologist, was 3.8 (IQR 1.2) minutes. The mean, predicted effect-site concentration of propofol at obstruction was 4.2±1.3 mcg/mL. The median saturation nadir during DISE was significantly higher (91.4±5.1% IQR) than that during standard sleep studies (81.0±11.25% IQR, both paired and unpaired t-test P<0.0001). FIG. 3 depicts the histogram plot of the distribution of saturation nadirs during polysomnography and DISE for analyzed patients (n=97). In FIG. 3, bin widths are 4.2% for polysomnography and 2.6% for DISE.

Saturation nadirs were lower during polysomnography than DISE in all but 7 patients; in that sub-cohort, median nadirs were 89.3% and 85%, respectively. Correlation analysis was performed with Spearman's rho for saturation nadir during DISE and BMI, AHI, age, and propofol effect-site concentration at obstruction. The 95% confidence intervals included zero in all cases, but the correlation between predicted propofol effect-site concentration and saturation could be as low as −0.43.

All patients completed DISE, and there were no adverse events associated with the study.

DISE with midazolam was introduced more than twenty years ago in the United Kingdom. There are no standardized criteria for DISE interpretation but test-retest reliability and inter-rater reliability have been reported. Consistency of interpretation is high among experienced otolaryngologists.

A variety of anesthetic approaches have been described; with most relying on modifications of the originally reported midazolam regimen or propofol by TCI or manual bolus. In children, dexmedetomidine after sevoflurane induction has been reported, but no comparison studies on differential results between anesthetic techniques have been published.

DISE is a niche procedure with a growing number of clinical reports in the literature. In the typical scenario a surgeon decides to implement the practice and requests anesthesiology to perform the anesthesia within a narrow range of anesthetic depth. The average practicing anesthesiologist will have limited experience with the gradual titration of propofol to the specific endpoint of airway obstruction without unintentional overdose necessitating airway intervention. The study population in Example 1 includes patients with high AHI who failed CPAP therapy. According to guidelines issued by the American Academy of Sleep Medicine, patients with an AHI greater than 30 (i.e. more than 30>10 s episodes of apnea or hypoventilation per hour) have severe OSA. Previously described DISE approaches with propofol are not without risk. Reports of desaturation requiring bag-mask ventilation are not uncommon with manual propofol titration even in patients with only moderate disease. Indeed, in a recent study comparing TCI to manual propofol bolus 65% of patients in the manual group demonstrated "sedation instability" compared to 5% in the TCI group. In contrast to the present study, those investigators excluded higher risk patients with BMI>30, presumably over concern for oxygen desaturation, and the mean AHI of study subjects was 21±7. Most reports using propofol for DISE have focused on surgical assessment or diagnostic utility and have not reported oxygen saturation profiles to the extent characterized here. The effective sedation seen in this study with a low rate of desaturation and infrequent need for airway support is an important result. The lowest saturation measured in this study (patients received oxygen at 2 liters per minute via oral cannula) was 74 percent. The mean oxygen saturation value was significantly higher than the mean during polysomnography and was comparable to that reported during TCI infusion. Supplemental oxygen is rarely used during polysomnography studies. It is acknowledged that the use of supplemental oxygen decreases the sensitivity of pulse oximetry to detect hypoventilation, but neither oxygen saturation nor hypoventilation were used as detection criteria during DISE. Few anesthesiologists would withhold supplemental oxygen from obese patients with severe sleep apnea during deep sedation with propofol without a compelling reason to do so. Conversely, few sleep centers would insist on supplemental oxygen during a sleep study as an essential safety measure. The comparison is made to demonstrate that the risk of desaturation during DISE is lower than that during a sleep study under normal practices. The extent of desaturation in obese patients with OSA is multifactorial. In addition to obstruction or apnea, loss of functional residual capacity during sleep, and the balance of metabolic rate and oxygen delivery under the effects of propofol also play a role.

Controlled infusion of propofol based on several competing pharmacokinetic models has been proposed to reduce the variability of anesthetic technique and rate of desaturation. TCI approaches have generally evidenced good reliability but require slow titration and the optimal pharmacokinetic model in the severe OSA population has not been rigorously demonstrated. Predicted effect-site concentrations between 2.0 µg/ml and 4.8 µg/ml to achieve obstruction have been reported with the Schnider or Marsh propofol models. The predicted effect-site concentration for obstruction that was observed (4.2±1.3 µg/mL) when using the Cortinez model (and adjoining an effect compartment with a $k_{e0}$ determined to yield the time to peak propofol effect of 1.6 minutes) is in a range of similar magnitude. There may well be a significant difference between the "true" effect-site concentrations and those modeled with the disclosed methods and systems. Since the predicted effect-site concentration is also likely to be rapidly changing at the time of obstruction, the precision of the predicted concentration may also be reduced. Rather than determine the "true" effect-site concentrations or even a target that could be generalized to other systems, Example 1 is directed to evaluating the fidelity of the disclosed hybrid Cortinez-Johnson pharmacokinetic/pharmacodynamic model to efficiently and reproducibly obtain conditions for DISE assessment while avoiding significant oxygen desaturation. Since unlike TCI, the practitioner need not make a preliminary guess as to the appropriate target, an effective strategy is more important than an accurately predicted effect-site concentration.

TCI may yield results that are superior to bolus techniques and may be easier to standardize. An important premise of the overall project is to create a system that reduces the reliance on provider experience to estimate manual titration requirements in the context of the lack of TCI approved devices in North America. This issue was addressed by devising a system that required few interactions with the pump, making it feasible for the anesthesiologist to observe the patient while titrating propofol to the clinical endpoint. The modeling system does not require a physical connection to the pump, since the user does the programming. The system is thus compatible with any pump capable of delivering a propofol bolus and infusion. For clinical efficiency and patient comfort the time to complete the procedure is also an important variable.

In one study by DeVito et al., (*Eur. Arch. Otorhinolaryngol* (2010), DOI 10.1007/s00405-010-1376-y) the average time for the procedures was 15.2 minutes in TCI group and 6.2 minutes in the manual control group. The mean time to obstruction employing the control system according to Example 1 was 3.9 minutes, which is comparable to the manual approach and substantially faster than with TCI control in published studies.

The disclosed system is able to achieve the endpoint of obstruction in a time similar to that reported by De Vito for bolus propofol, without the associated incidence of desaturation requiring intervention that was noted.

A propofol infusion strategy that requires limited experience with propofol dose selection and only one pump dosing change reliably produced airway obstruction in patients with severe sleep apnea undergoing DISE. The reported system produced clinical obstruction faster than TCI based systems for similar procedures reported in the literature with a clinically acceptable rate of desaturation when compared to polysomnography in the same individuals.

Figure 4:
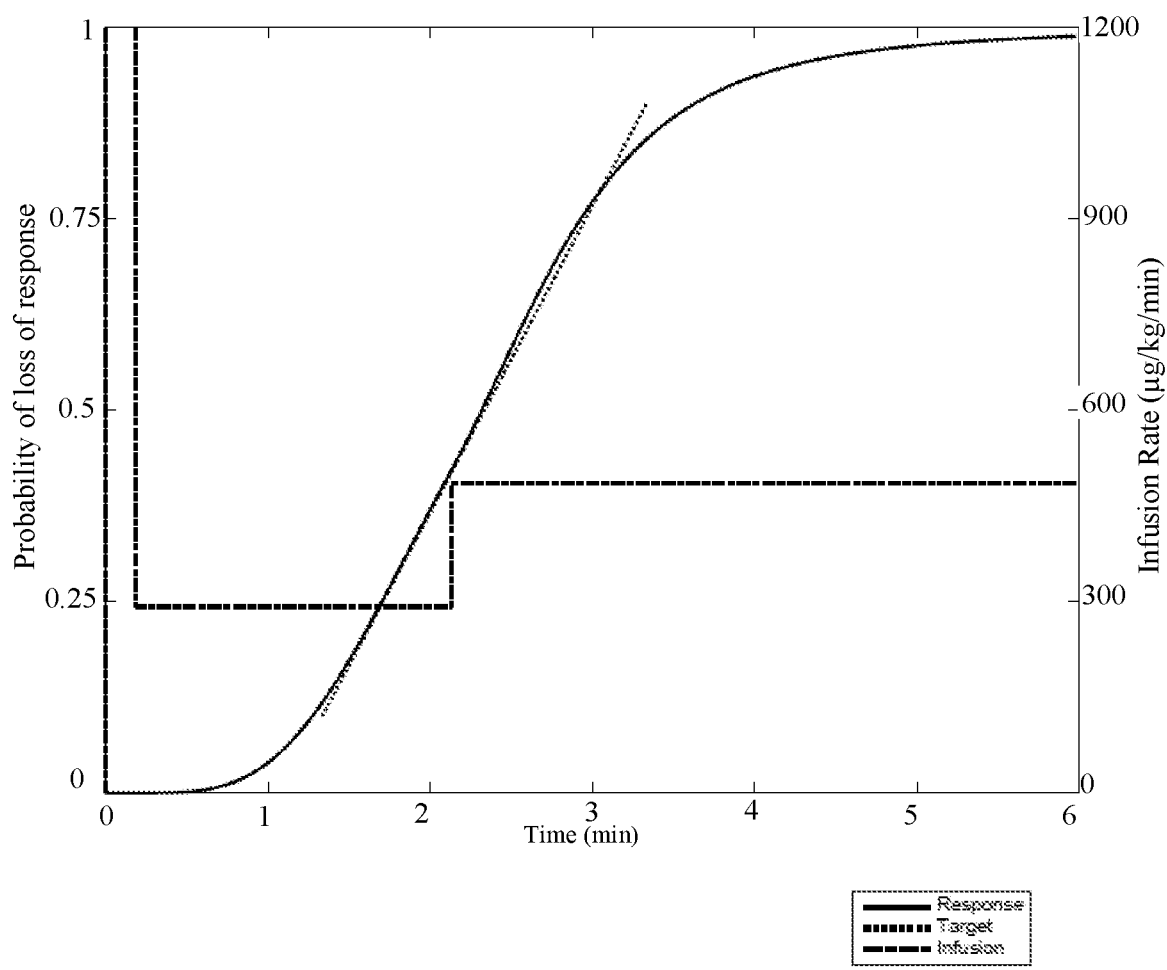
FIG. 4 is an exemplary graph showing infusion rate and probability of loss of response over time.

The purpose of the control system is to determine an infusion sequence that will cause a linear increase in the probability of sedation over a defined interval that will be similar for all weights and ages of patients, as illustrated in FIG. 4. The sequence is comprised of an initial bolus, an initial infusion rate, a secondary infusion rate, and a time at which this transition occurs. This permits the operator to set up the pump with the first two values prior to initiation of sedation and only make a single change in infusion rate at a specified time to complete the procedure.

To accomplish this, three components are utilized:
1) A pharmacokinetic model of propofol
2) A pharmacodynamics model of propofol
3) A minimization of trajectory error The purpose of the pharmacokinetic model is to translate drug administration into effect-site concentration. While several models of propofol have been described, the model of Cortinez et al. is utilized, as it does not suffer from the limitations of the calculation of lean body mass. Model parameters were taken from Table 2 of that publication. A biophase compartment is adjoined to this model, calculating $k_{e0}$ so that the time to peak effect is 1.6 minutes. The MATLAB® code for the state space model with observation of the effect-site concentration can be found on the OpenTCI website.

Given an infusion sequence I (comprised of a bolus (B), an initial infusion ($I_1$), a second infusion ($I_2$), and a time for transition from $I_1$ to $I_2$ ($T_1$), the effect-site concentration for propofol is given by equation A1:

$$C_e(t)=PK(B,I_1,I_2,T_1) \qquad \text{A1}$$

Where $C_e(t)$ is the effect-site concentration at time t and PK is the pharmacokinetic model with the adjoined effect-site compartment.

The purpose of the pharmacodynamic model is to determine the probability of a clinical event given an estimated effect-site concentration. The model of Johnson et al. is employed. This model considers both propofol and remifentanil and provides response probability predictions for four different levels of stimulation; the parameters for loss of responsiveness were employed with remifentanil set to zero, as shown in equation A2:

$$P(t) = \left(\frac{C_e(t)/C_{50}}{1 + C_e(t)/C_{50}}\right)^n \quad \text{A2}$$

In equation A2, $C_{50}$ is the effect-site concentration associated with a 50% probability of loss of responsiveness and n is the steepness of the curve.

FIG. 4 illustrates sedation of a 48-year-old patient weighing 100 kg. The propofol infusion rate is depicted as a dashed line: a bolus of 365 µg/kg (36.5 mg over 11 seconds) followed by an initial infusion of 154 µg/kg/min for 117 seconds (delivering 57 mg), followed by an increase to 486 µg/kg/min. The probability of unresponsiveness for the patient is depicted as a solid line. The dotted line is the target (the desired trajectory of response probability). The trajectory is a line of increasing probability, indicated as "Target" in FIG. 4. The line starts at a 10% probability at 80 seconds, and ends at 90% probability at 200 seconds. The trajectory error is the difference between the predicted response probability for a given infusion sequence and the trajectory. The infusion sequence (B, $I_1$, $I_2$, $T_1$) that results in the minimum value for trajectory error is identified by a simplex minimization using the MATLAB® Optimization Toolbox.

Figure 5:
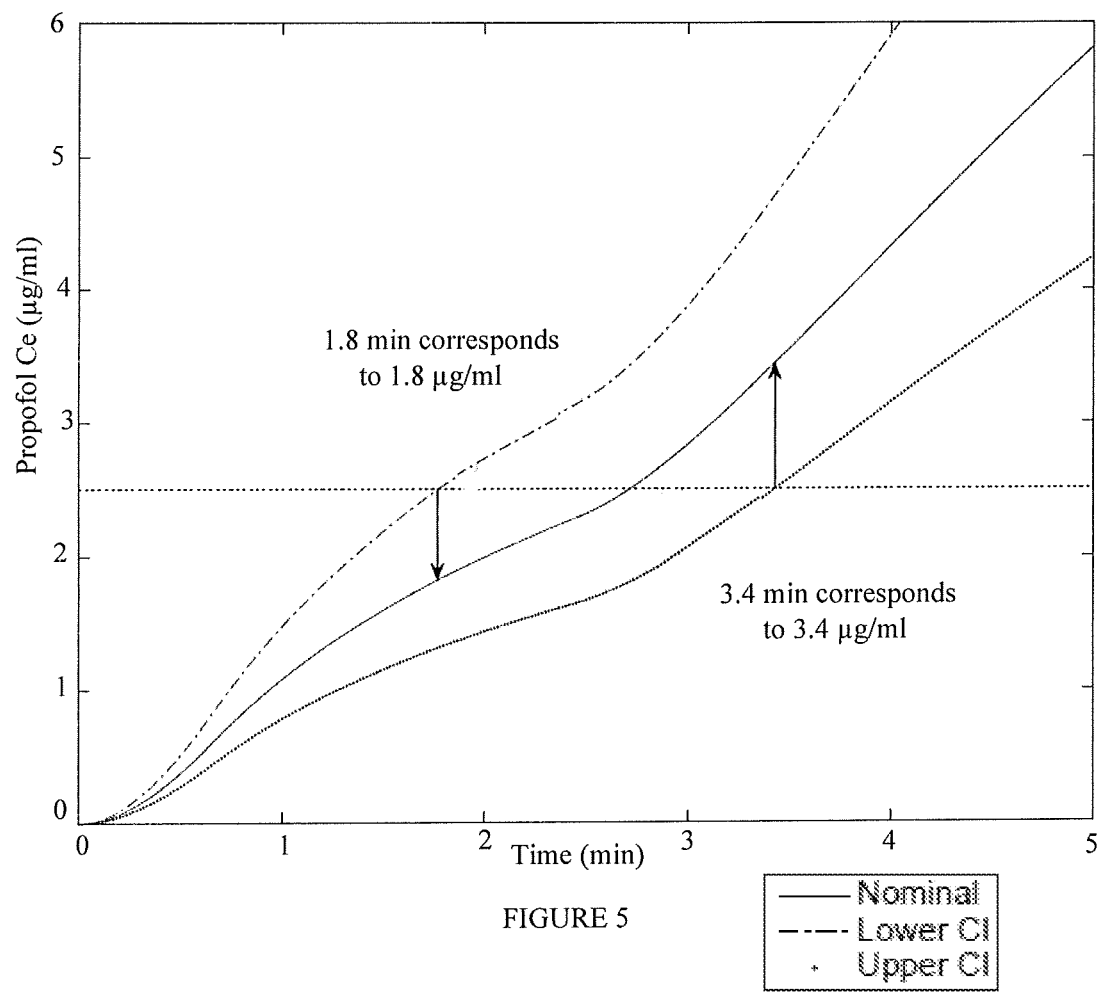
FIG. 5 is an exemplary graph showing propofol concentration over time.
Figure 6:
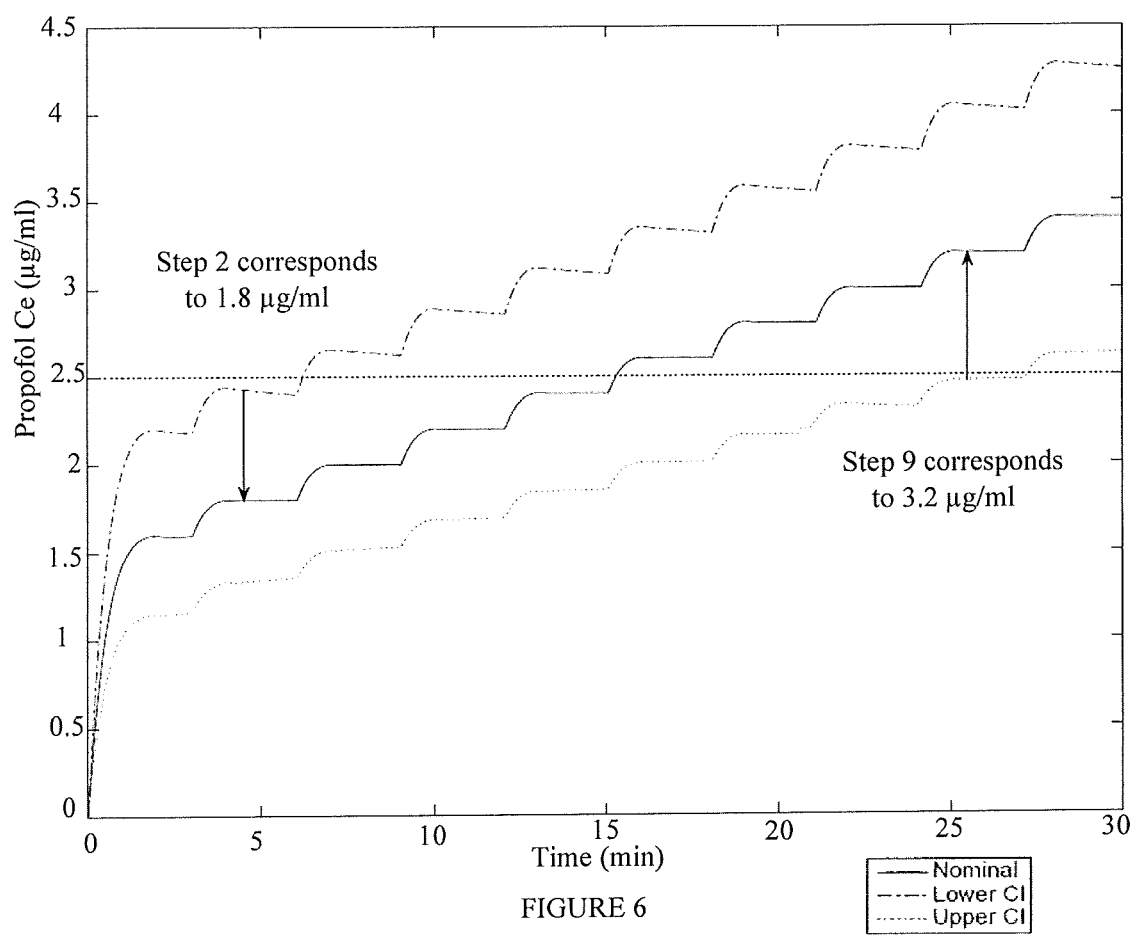
FIG. 6 is an exemplary graph showing propofol concentration over time.

Any open loop method will be affected by modeling errors. Consider the result of varying all of the parameters of the nominal Cortinez model by half of the 95% confidence intervals, yielding two additional models termed "Upper CI" and "Lower CI". The parameters of these models are listed in Table 2. Assume that the endpoint of obstruction will be achieved at an effect-site concentration of 2.5 µg/ml. The application of the infusion sequence determined for the nominal parameters to the three models is depicted in FIG. 5. FIG. 5 shows application of the infusion sequence designed for a patient with nominal parameters to the nominal (solid line), upper CI (dotted line), and lower CI (dot-dash line) patients. Obstruction occurs at 2.5 mg/ml, but the onset is at 1.8 minutes in lower CI and 3.4 minutes in upper CI, leading to misidentification of the effect-site concentration associated with obstruction. The lower CI model responds more quickly (having lower volumes and clearances), and obstruction will be observed after 1.8 minutes, which would correspond to an effect-site concentration of 1.8 µg/ml under the assumption that the patient followed the nominal model. Similarly, the upper CI model will not reach obstruction until 3.4 minutes, corresponding to an effect-site concentration of 3.4 µg/ml. Compare this result to application of a target controlled infusion designed for the nominal model. Starting with an effect site target of 1.6 µg/ml, the target was increased by 0.2 µg/ml every three minutes, as depicted in FIG. 6. FIG. 6 shows application of a target controlled infusion designed for a patient with nominal parameters to the nominal (solid line), upper CI (dotted line), and lower CI (dot-dash line) patients. Obstruction occurs at 2.5 µg/ml, but the onset follows the second step in lower CI and the 9th step in upper CI, leading to misidentification of the effect-site concentration associated with obstruction. The lower CI model will achieve obstruction after the second step, corresponding to an effect-site concentration of 1.8 µg/ml, while the upper CI model will achieve obstruction after the 9th step, corresponding to an effect-site concentration of 3.2 µg/ml. While the impact of parameter error on the error in the identified effect-site concentration is minimal, the time required to arrive at obstruction is considerably longer, 6.2 to 27.25 minutes with the TCI approach versus 1.8 to 3.4 minutes with PRC. Additionally, the TCI approach requires multiple adjustments of the target concentration, while PRC only requires a single adjustment. Thus, PRC reduces the effort of both the endoscopist and the anesthesiologist without a significant reduction in precision in the determination of the effect-site concentration associated with obstruction.

TABLE 2

Model parameters for the three simulated patients used in FIGS. 5 and 6.

| Parameter | Nominal | Lower CI | Upper CI |
|---|---|---|---|
| V1 (L) | 4.5 | 3.5 | 5.2 |
| V2 (L) | 26.6 | 15.7 | 32.6 |
| V3 (L) | 53.8 | 42.4 | 309.9 |
| CL1 (L/min) | 2.2 | 1.9 | 2.4 |
| Q2 (L/min) | 3.2 | 2.1 | 4.2 |
| Q3 (L/min) | 0.52 | 0.49 | 1.14 |

Example 2

Probability Ramp Control Vs. CRNA Dosing of Propofol for EGD

Endoscopic sedation typically requires titration of propofol to an endpoint of deep sedation with limited overshoot into general anesthesia. This is typically accomplished by intermittent boluses of propofol followed by an infusion to maintain the desired state. Considerable pharmacodynamic variability has been demonstrated for propofol, and regimens that target a low probability of patient response may produce intolerable ventilatory depression. Nonetheless, experienced anesthesia providers routinely titrate propofol to the desired effect, presumably by observing the clinical response and adjusting their dosing accordingly. While this skill can be acquired with practice, this process is time-consuming and expensive. Despite considerable information on the pharmacokinetics of propofol, practitioners do not typically employ pharmacokinetic modelling in endoscopic sedation, relying on empirically derived dosing strategies and the ability to rescue oversedation with airway maneuvers. A system that reduces the necessity for active involvement of experienced practitioners would be a useful step towards lowering the cost of endoscopic sedation, which could exceed 5 billion dollars annually in the US. To be useful, such a system would need to reduce the complexity of the pharmacokinetic task and decrease the frequency of intolerable respiratory depression.

Previous work demonstrated in simulation that incorporating a single clinical observation into the control process can decrease the combined pharmacokinetic-pharmacodynamic error by a factor of three compared to using target controlled infusion for a population average (Mandel & Sarraf, *Anesth Analg.* 2012; 114:1221-9). This approach may be termed Probability Ramp Control (PRC). One of the inventor's hypotheses was that PRC would provide equivalent depth of sedation to that obtained by experienced anesthesia providers. Another of the inventor's hypotheses was that PRC would require fewer adjustments in control, a lower rate of ventilatory depression, and lower frequency of arterial desaturation.

With written informed consent, 40 patients 18 years of age and older scheduled for elective esophagogastroduodenoscopy (EGD) with monitored anesthesia care who had no contraindications to propofol were randomly allocated to two groups in an open label design. In an endoscopy unit, monitored anesthesia care was provided by certified registered nurse anesthetists (CRNAs) supervised by an attending anesthesiologist; every CRNA involved in the study had a minimum of 6 months experience in endoscopic sedation; all studies were conducted when an investigator was present in the endoscopy suite. In addition to ASA standard monitors, respiratory inductance plethysmography (RIP) (Ambulatory Monitoring Inc, Armonk, N.Y.), SEDLine® patient state index (PSI) (Masimo Corp, Irvine, Calif.) and RAD87 pulse oximeter (Masimo Corp, Irvine, Calif.) were applied. All patients received 50 μg of fentanyl immediately prior to initiation of sedation. In the control arm, the CRNA assigned to the case titrated propofol until the patient could tolerate insertion of a Robertazzi nasopharyngeal airway without purposeful movement, then set the infusion rate for maintenance on an Alaris Medley infusion pump. Propofol dosing was recorded by an investigator. In the experimental arm, patient age and weight were used by the PRC algorithm to calculate bolus, infusion1, infusion2, and time for transition from infusion1 to infusion2. These numbers were reviewed by an investigator prior to initiation of sedation, and when the patient could tolerate airway placement, the software determined the maintenance infusion to maintain the effect-site concentration at the value existing at that time. Custom software written in Labview 2012 (National Instruments, Austin, Tex.) performed these calculations, transmitted the infusion rates to a Graseby 3400 pump (Marcal Medical, Millersville, Md.), and acquired data from the monitors. Propofol administration was determined by querying the pump for infused volume to avoid limitations of the Graseby 3400 pump.

All patients were preoxygenated using a Mapleson circuit at oxygen flows greater than 10 liters per minute. Following placement of the Robertazzi airway, the Mapleson circuit was connected to the airway via the connector from an endotracheal tube and the adjustable pressure limit valve closed, assuring continuous flow of 100% oxygen into the hypopharynx.

Figure 7:
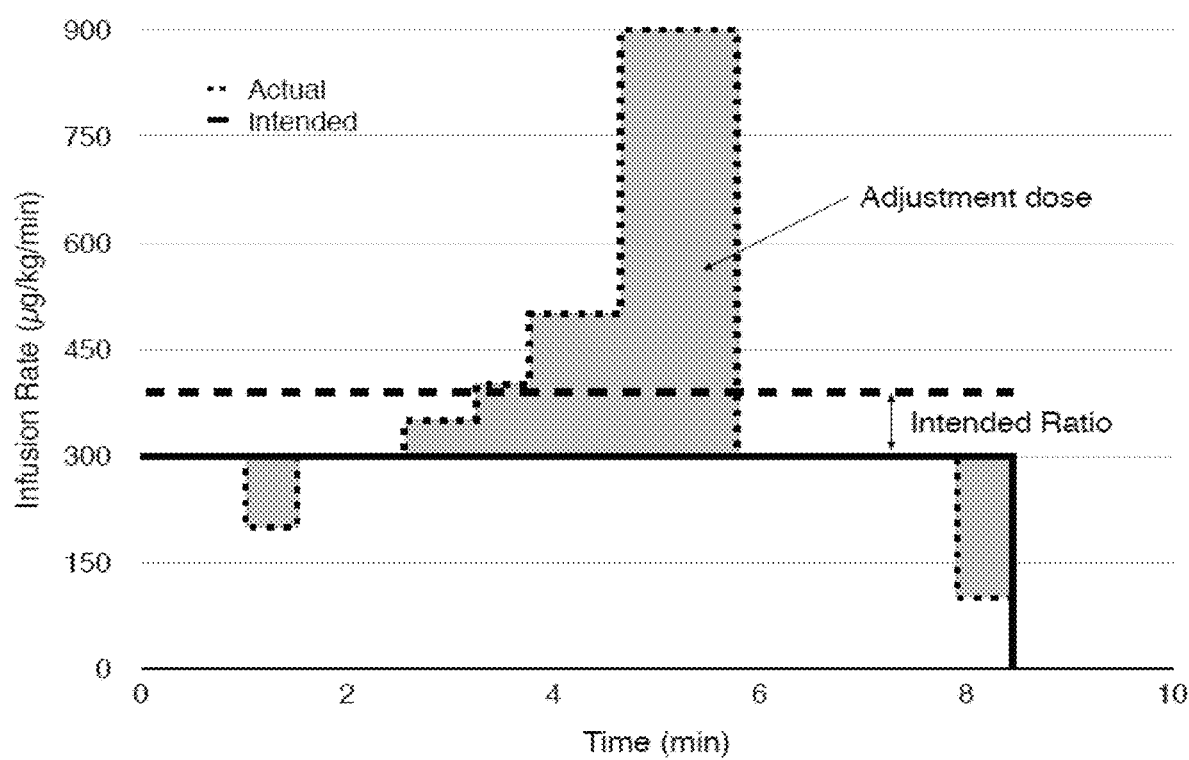
FIG. 7 is an exemplary graph illustrating an intended trajectory.

In control patients, the CRNA was free to alter the infusion rate up or down, or give additional boluses if, in their judgement, these were required. In experimental patients, the CRNA could request additional boluses or changes in infusion rates as they saw fit. In addition to the total dose of propofol, the initial bolus, and the initial infusion rate, an additional derived measures was defined—the intended trajectory. This measure is the amount of propofol that would have been delivered if the infusion rate was fixed at the value specified at the time of insertion of the nasopahryngeal airway, excluding all subsequent changes in infusion rate and additional boluses. This measure is reported in two ways. The first is termed "adjustment dose", which is the cumulative absolute value of the difference between the intended trajectory and the actual administration. The second is the "intended ratio", which is the ratio of the dose delivered on the intended trajectory and the actual administration. These measures are depicted in FIG. 7. In FIG. 7, the dotted line indicates the actual infusion rates, while the solid line indicates the intended trajectory (fixing the infusion rate at 300 μg/kg/min). The adjustment dose is represented as the gray shaded area, and the intended ratio is the ratio of the intended trajectory (300) to the mean of the actual administration (dashed line at 390 μg/kg/min); 0.77.

The intent of the first measure is to quantify the active involvement of the CRNA in maintaining the desired trajectory (with the ideal value being zero), while the second measure is intended to quantify how close the actual requirement was to the initial estimate of propofol requirement (with the ideal value being one).

Ventilatory depression was assessed from respiratory inductance plethysmography signals. The signals were filtered by ensemble empirical mode decomposition employing 450 realizations and noise scaled to 40% of signal power. The dominant mode was used for the Huang-Hilbert Transform (HHT). Minute ventilation was computed as the product of the respiratory rate times the magnitude of volume change at one second intervals. Baseline ventilation was determined from several breaths prior to initiation of sedation; subsequent measurements were normalized by this baseline value. These values were grouped into one minute epochs and the median of values less than 100% obtained. Values above 100% were excluded for two reasons. First, periods of obstruction were typically followed by compensatory increases in ventilation; 20 seconds of apnea followed by 40 seconds of hyperventilation is not the same as 60 seconds of normoventilation. Second, hyperventilation was a common response to inadequate sedation; one patient exhibiting hyperventilation and another exhibiting apnea in the same minute is not the same as two patients exhibiting moderate hypoventilation over the same interval.

Oxygen saturation was acquired from the RAD87 at one second intervals, as was the patient state index. Obvious artifacts such as sensor dislodgement were excluded from analysis. Desaturation is reported as cumulative time below specified saturation in the range from 54% to 90%.

Effect site estimates were calculated using the Cortinez model employing the nominal values, with an adjoined effect compartment. The $k_{e0}$ was chosen to yield a time to peak effect of 1.6 minutes. MATLAB® code for the state-space implementation of this model with observation of the effect site is available on the OpenTCI website.

Power analysis was based on a previous study of endoscopic sedation, in which the mean and standard deviation of BIS® values for anesthetist-administered propofol sedation were 72.1±15.1. In this study, the average procedure time was 29.3 minutes. While BIS is comprised of a moving window of 60 seconds of data, successive data points may be correlated, indeed, the mean autocorrelation of BIS at a 60 second lag was 0.91. Thus, the number of independent observations per patient lies between 2.6 and 29.3. A study comprised of 40 patients would have a power of between 80% and 98% for detecting a difference of 5 points in the BIS score with a P of 0.05. While BIS and PSI do not yield identical numbers during propofol administration, it was assumed that patients who could not be distinguished by SEDLine® would not have been distinguished by BIS.

All continuous variables were assessed for normal distribution with the Lilliefors test; normally distributed variables were compared with unpaired T-test, non-normally distributed variables by Mann-Whitney U test, binomial outcome differences by Fisher's exact method, and confidence intervals for binomial outcomes by the Clopper Pearson method. Correlation between actual, intended, and discretionary propofol doses and age and weight were determined by Spearman's Rho, with 95% confidence intervals estimated by Fisher's method. All analysis was performed using the Statistics toolbox in MATLAB® 2013b (Mathworks, Natick, Mass.).

All patients completed their procedures without significant movement. There were zero (95% CI 0-1.76) adverse events in the experimental arm; in the control arm, one (95% CI 0.004-5) patient required bag-mask ventilation due to desaturation in response to the initial bolus. No patient or endoscopist-rated satisfaction with care below neutral. Usable respiratory data was collected from 39 of the 40 patients.

Figure 8:
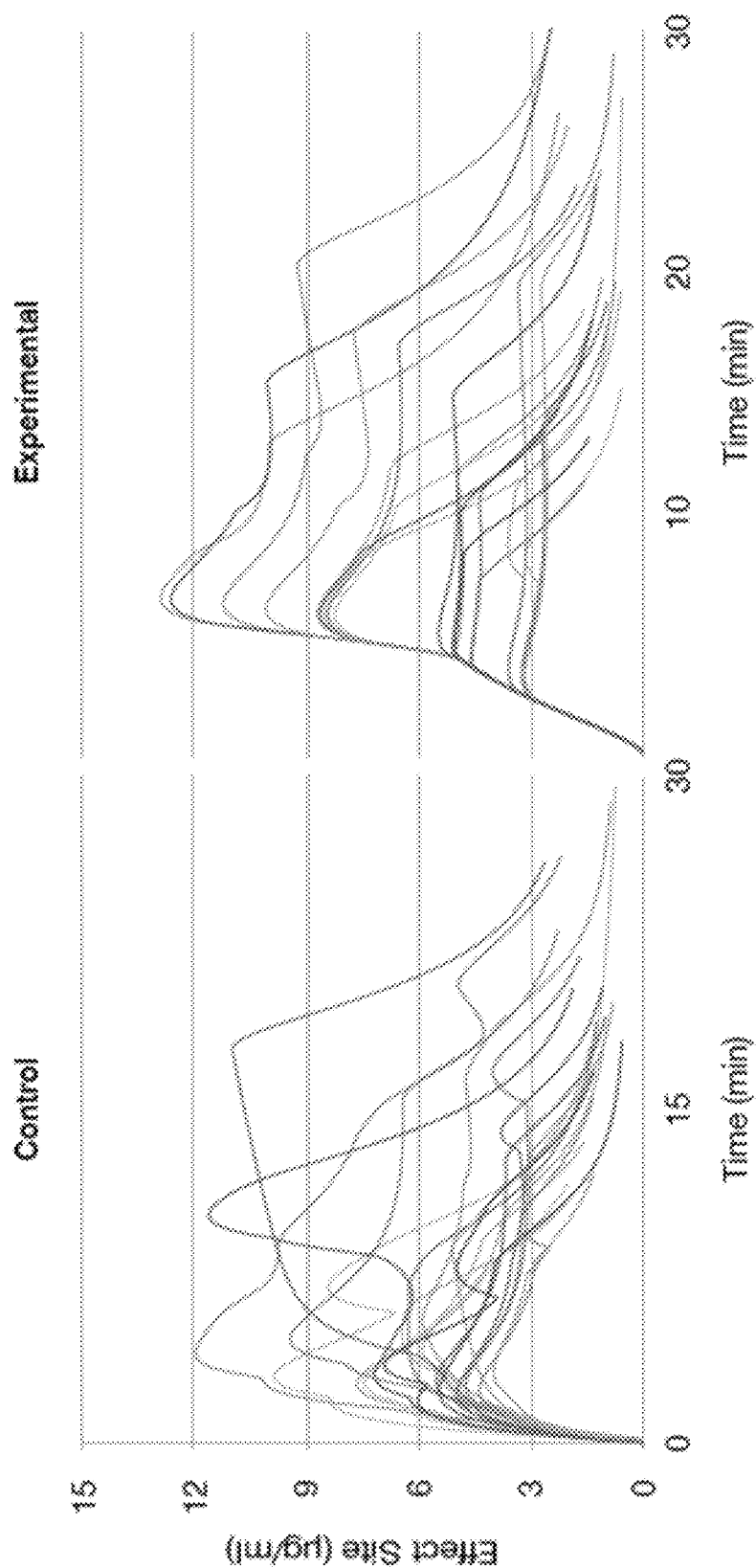
FIG. 8 includes exemplary graphs illustrating effect-site concentration trajectories for the control group (left panel) and the experimental group (right panel).
Figure 10:
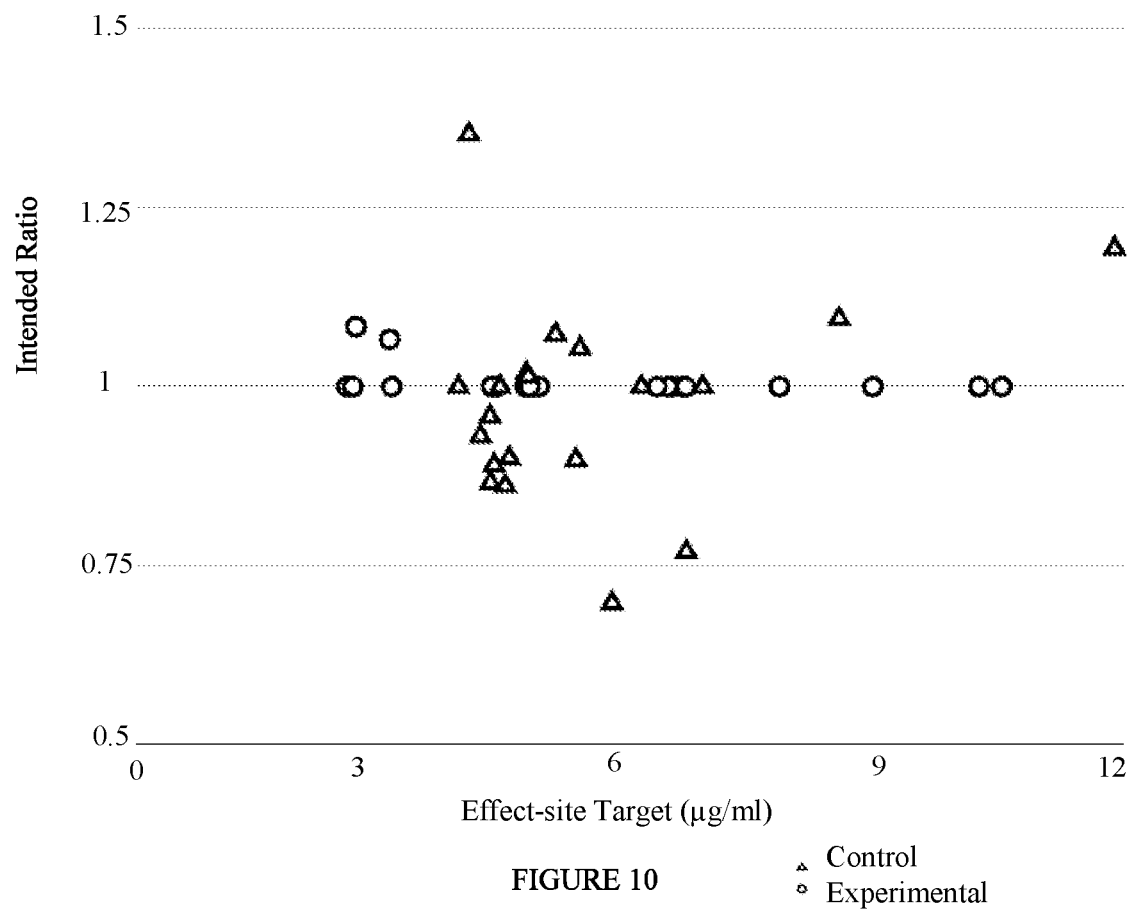
FIG. 10 is an exemplary scatter plot illustrating the intended ratio versus the effect-site at target.

Patient characteristics are presented in Table 3. There were no significant differences between groups in weights, ages, or procedure times. Total propofol dose and average SEDLine® patient state index were similar, as were estimates of effect-site concentration at both the time of loss of responsiveness to nasopharyngeal airway placement (target) and at peak. In the control group, dosing adjustments were required in a larger number of patients, and the total amount of propofol used in these adjustments was greater. The intended ratio was close to one in both groups, but more variable in the control group, as portrayed in FIG. 10, which is a scatter plot illustrating the intended ratio to the effect-site concentration associated with loss of responsiveness to nasopharyngeal airway placement (target). In FIG. 10, control patients are indicated as triangles; experimental patients as circles. Individual effect-site trajectories are depicted in FIG. 8, derived by applying the administered propofol to the Cortinez model with adjoined effect site compartment. The greater variability in trajectories in control vs. experimental patients is evident.

TABLE 3

Patient characteristics. No significant difference for age, weight, procedure time (unpaired Student's T test), number of males, or number of ASA 3 (Fisher's exact).

|  | Control | Experimental |
|---|---|---|
| Age | 48.5 (14.2) | 52.8 (16.5) |
| Male | 12 (60%) | 7 (35%) |
| ASA | 3/10/7 | 5/7/8 |
| Weight | 82.3 (27.4) | 82.1 (23.9) |
| Procedure Time | 9.03 (3.75) | 8.90 (4.79) |

Rank correlation of propofol doses and age and weight in the control arm are listed in Table 5.

A weak correlation between the first infusion and weight is seen; since the CRNAs uniformly entered infusion rates into the Alaris pump in units of µg/kg/min, correlation is expected; indeed, had every patient been set to the same infusion rate, the correlation would be 1.0. No significant correlation was seen between total dose or first bolus and weight or age.

Figure 9:
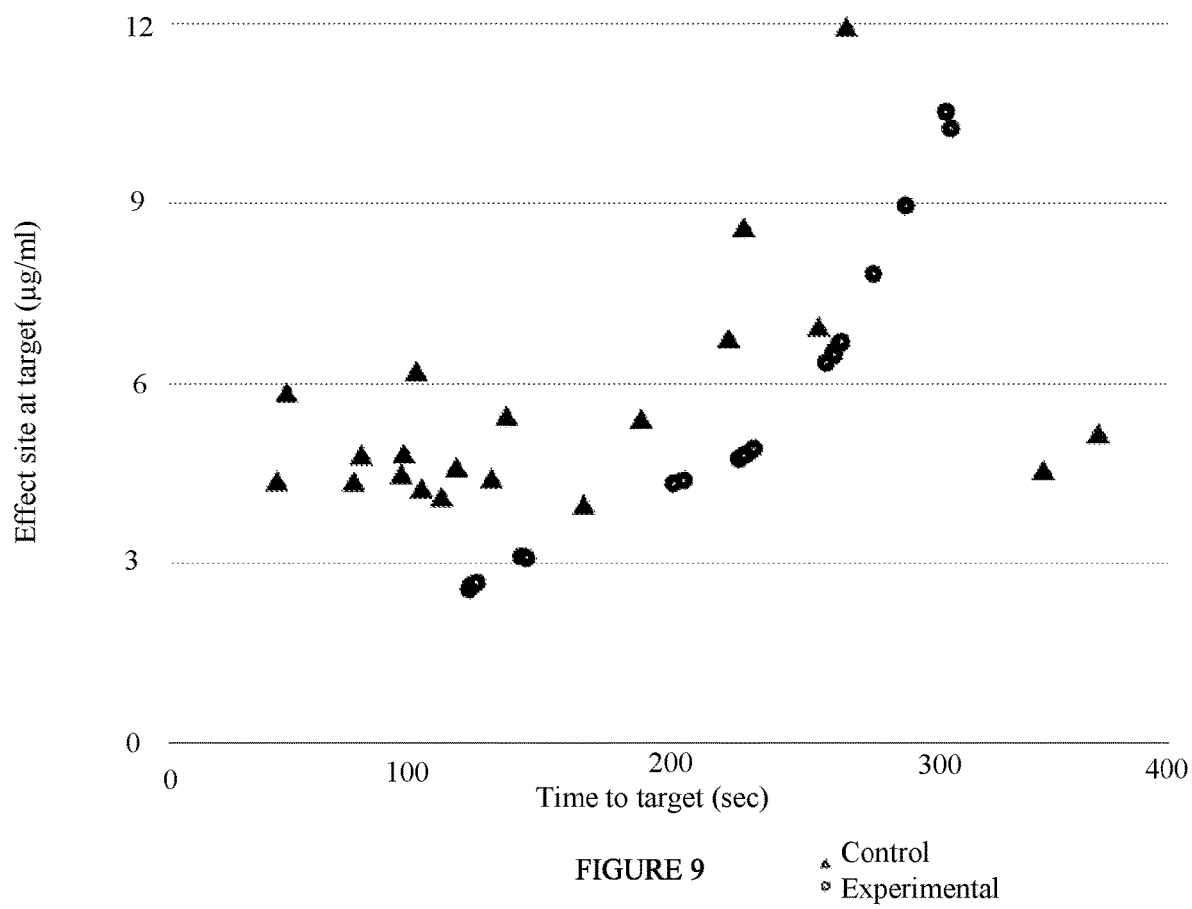
FIG. 9 is an exemplary scatter plot illustrating effect site at target versus time to target.

The time to achieve the target versus the target value is depicted in FIG. 9, which is a scatter plot relating the effect-site concentration associated with loss of responsiveness to nasopharyngeal airway placement (target) with the time required to achieve this concentration. In FIG. 9, control patients are indicated as triangles; experimental patients as circles. In the control group, patients achieved the target more rapidly, 2 (2.2) vs. 3.9 (1.6) minutes. No control patients were identified at targets below 3.9 µg/ml, while 5/20 patients in the experimental group were identified at targets below this value. This is a direct consequence of the magnitude of the initial bolus in the control patients, which was 80 (35) mg.

Rank correlation between propofol doses and the effect-site concentration estimated at the time of nasopharyngeal airway placement is shown in Table 6. A weak correlation between first infusion and target was seen (p=0.51, P=0.02), but the first bolus, intended ratio and the adjustment dose were uncorrelated with the target. The relationship between intended ratio and effect-site concentration at the target is depicted in FIG. 10.

Figure 11:
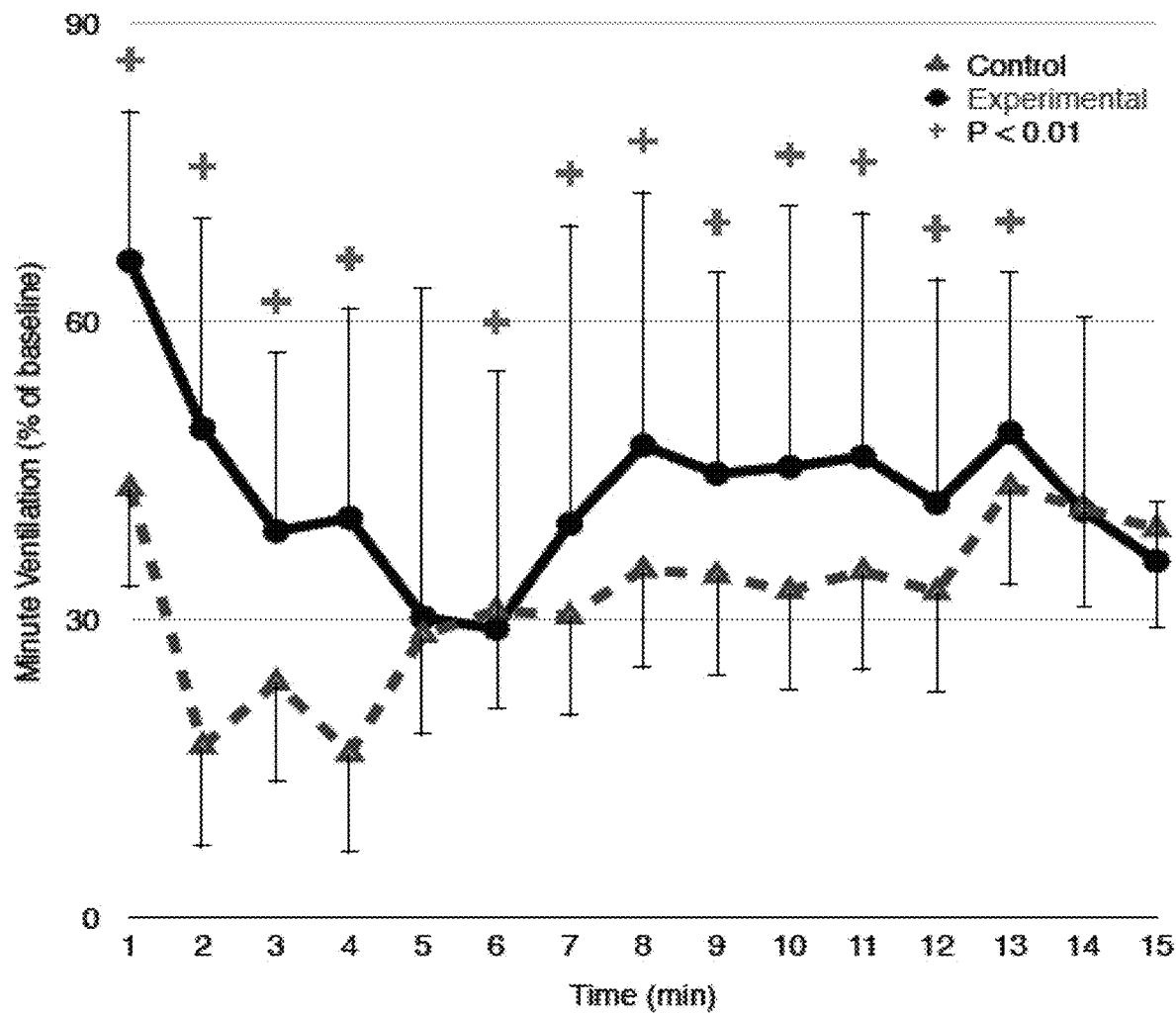
FIG. 11 is an exemplary graph showing ventilatory depression at one minute intervals.
Figure 12:
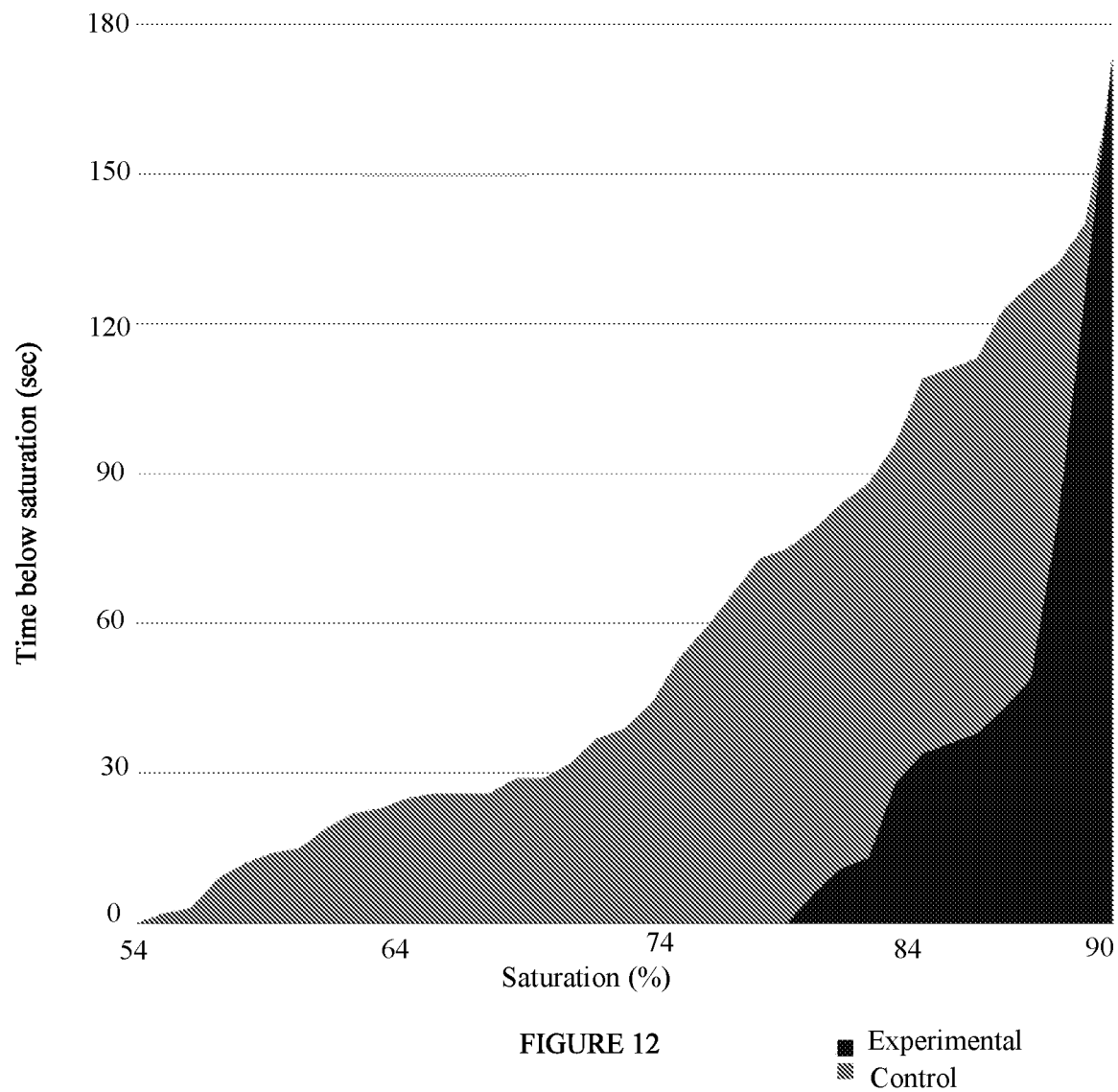
FIG. 12 is an exemplary graph showing cumulative time (in seconds) below a given saturation. Control patients are indicated in gray; experimental patients in black.

Ventilatory depression is depicted in FIG. 11, expressed as the percent of baseline minute ventilation. Control patients are indicated as triangles; experimental patients as green circles. Values are the median of all samples in the one minute epoch, and error bars depict quartile ranges. Control patients exhibited greater depression at all times except minutes 5-6 and beyond 13 minutes (which was typically in the recovery phase). Cumulative time below a given saturation is represented in FIG. 12. While values below 90% were observed in a minority of patients (3 control patients and 2 experimental patients, non-significant), for any value of oxygen saturation below 90%, control patients spent more time at or below that saturation. It should be emphasized that all patients were administered 100% oxygen via the Robertazzi airway; had the study employed nasal cannula oxygen at 2 liters per minute, more saturation values below 90% would be expected.

TABLE 4

Sedation characteristics. Effect-site concentrations estimated using Cortinez model with adjoined effect compartment. NS—No significant difference; # P < 0.001, * P = 0.028. All values except number of adjustments are median (IQR).

|  | Control | Experimental |
|---|---|---|
| Total Propofol (mg) | 295.6 (136.3) | 287.5 (167) NS |
| Cases with adjustments (#) | 16 | 2 # |
| Adjustment Dosing (mg) | 24.1 (37.2) | 0 (0) # |
| Intended ratio | 1.0 (0.14) | 1.0 (0) NS |
| Maximum Effect Site (µg/ml) | 6.1 (3.5) | 5.3 (4.6) NS |
| Target Effect Site (µg/ml) | 4.8 (1.6) | 4.9 (2.9) NS |
| Patient State Index | 41.2 (14.1) | 41.1 (23.5) NS |
| Time to target (min) | 2 (2.2) | 3.9 (1.6) * |

TABLE 5

Correlation coefficients (Spearman's ρ) for propofol administration quantities and age and weight in the control arm. Confidence intervals calculated by Fisher's method. First infusion (mg/min) is weakly correlated with weight; no other measures demonstrated significant correlations.

|  | Spearman's ρ | 95% CI | P |
|---|---|---|---|
| Total Dose vs. Weight | 0.28 | −0.18-0.64 | 0.2305 |
| Total Dose vs. Age | 0.23 | −0.24-0.61 | 0.3333 |
| First Bolus vs Weight | 0.23 | −0.23-0.61 | 0.32 |
| First Bolus vs Age | 0.03 | −0.42-0.47 | 0.9 |
| First Infusion vs Weight | 0.45 | 0.01-0.75 | 0.0448 |
| First Infusion vs Age | 0.09 | −0.37-0.51 | 0.7119 |

TABLE 6

Correlation coefficients (Spearman's ρ) for propofol administration quantities and the effect-site concentration at time of nasopharyngeal airway placement (target) in the control group. Confidence intervals calculated by Fisher's method. First infusion (expressed in µg/kg/min) and total dose are weakly correlated with target.

|  | Spearman's ρ | 95% CI | P |
|---|---|---|---|
| First Infusion vs Target | 0.51 | 0.09-0.78 | 0.0213 |
| First Bolus vs Target | −0.14 | −0.55-0.33 | 0.5681 |
| Total dose vs Target | 0.48 | 0.04-0.76 | 0.0351 |
| Intended dose vs Target | 0.37 | −0.09-0.70 | 0.1106 |
| Adjustment dose vs Target | 0.08 | −0.38-0.50 | 0.7470 |

This example demonstrates that observation of a single clinical event during a slow induction used to determine the maintenance infusion can provide control of propofol that is superior to that provided by experienced anesthesia providers by all measures except time to placement of the endoscope. While the PRC system took an additional 111 seconds to achieve endoscope placement, once control was achieved, significantly fewer adjustments were required to maintain patient compliance, and significantly less ventilatory depression and desaturation were noted. While an additional two minutes at the start of the procedure might seem a significant delay, the range of times to achieve sedation was narrower and sedation was not observed in the first two minutes in the experimental group. In the control arm, sedation and ventilatory depression were frequently seen in the first two minutes. This might influence the perception of gastroenterologists as to when they needed to be "on deck".

To understand this result, several features of administration of propofol in the control arm should be noted. First, the initial bolus of propofol was not correlated with weight or age. Conversely, age and weight were the only determinants of loading sequence in the experimental group; uncertainty in dosing requirement is completely displaced to the act of target identification. This does not mean that the CRNAs did not incorporate a priori knowledge into their choice of the initial dosing, merely that age and weight were not the largest factors in choice of bolus. Second, while the initial bolus of propofol given by the CRNAs yielded more rapid induction, this precluded identifying targets below effect-site concentrations of 3.9 μg/ml, which comprised 20% of the experimental group. While the consequences of utilizing an effect-site concentration of 3.9 μg/ml on a patient who would be unresponsive at 2.6 μg/ml are unknown, there may be utility in using the lowest possible dose. Third, while there was a weak correlation between the first infusion and the identified target, and the intended ratio was, on average, one, there was considerable variability in the intended ratio and a requirement for adjustment dosing in most patients the control arm. In the experimental arm, there was little need for adjustment dosing. Fourth, intended ratio and adjustment dosing were uncorrelated with target, suggesting that outliers in propofol sensitivity were not responsible for the differences between groups.

PRC provides an advantage over target controlled infusion (TCI). With TCI, it is possible to increase the target in incremental steps, allowing the effect-site to approach equilibrium before initiating the next step. Starting at 2.6 μg/ml, taking two minutes at each step, with each step a 1 μg/ml increment, the median patient in the experimental group would be sedated in 8 minutes, twice as long as was required for PRC. The estimated effect-site concentration derived from this approach will be subject to the same modelling errors as PRC, and will be quantized to 1 μg/ml accuracy.

By using the infusion pump to deliver the initial bolus over a longer time and inferring the maintenance dose from the dose delivered at loss of responsiveness, it might be possible to mimic certain behaviors of PRC. However, a limitation to this strategy is that the selection of the maintenance infusion is not a linear transformation of the induction dose.

PRC differs from SEDASYS®. SEDASYS requires a user to request an increase in propofol administration, and limits the dose by loss of response to the automated response monitor, ventilatory depression detected by capnography, and desaturation detected by pulse oximetry. In contrast, PRC increases the propofol concentration until the user indicates that the clinical endpoint has been achieved, and then maintains this effect-site concentration. PRC can be used to achieve any depth of sedation that can be identified as a transition by the clinician, including general anesthesia, as was the approach taken in this example. While loss of response to the automated response monitor could be used as the target for PRC to achieve light sedation, use of SEDASYS to produce general anesthesia is inconsistent with its labelled indications.

While ventilatory depression was less frequent in the experimental group compared to the control group, there were still patients in the experimental group for whom airway manipulation was performed, and in whom saturations below 90% were observed. Additionally, the use of the Robertazzi airway and 100% oxygen likely reduced the incidence of desaturation despite the decreases in minute ventilation. The study does support the notion that PRC can reduce the work associated with endoscopic sedation, permitting a staffing model in which anesthesia providers manage more than a single patient simultaneously. This is analogous to management of labor analgesia, in which a single provider manages multiple patients simultaneously. If a profoundly toxic drug such as bupivacaine can be safely administered to a high risk population such as parturients, it is not unreasonable to suggest that the same level of safety can be achieved with propofol. The utilization of anesthesia providers to administer propofol to low risk patients has come under increasing scrutiny, and it has been suggested that charges associated with this practice may exceed the perceived value. While the system in this exemplary embodiment utilized direct connection of a computer to a Graseby 3400 pump, the system also can be implemented by entering values on a computer screen manually into a variety of infusion pumps, albeit with reduced accuracy.

Example 3

Probability Ramp Control Vs. CRNA Dosing of Propofol for EGD

According to this Example 3, it was demonstrated that by incorporating the observation of a transition to a clinical endpoint into a control loop, the error in maintaining this clinical endpoint is reduced in comparison to targeting an effect site estimate associated with the 50% probability of achieving the endpoint (Mandel & Sarraf, *Anesth Analg.* 2012; 114:1221-9). A limitation of this method is the propriety of the pharmacokinetic-pharmacodynamic (PKPD) models, which are derived from small numbers of volunteers in a research setting using infusion sequences and clinical endpoints different from those in clinical care. This example describes an embodiment for generating and using data from large groups of patients undergoing clinical care to refine PKPD models.

Figure 13A:
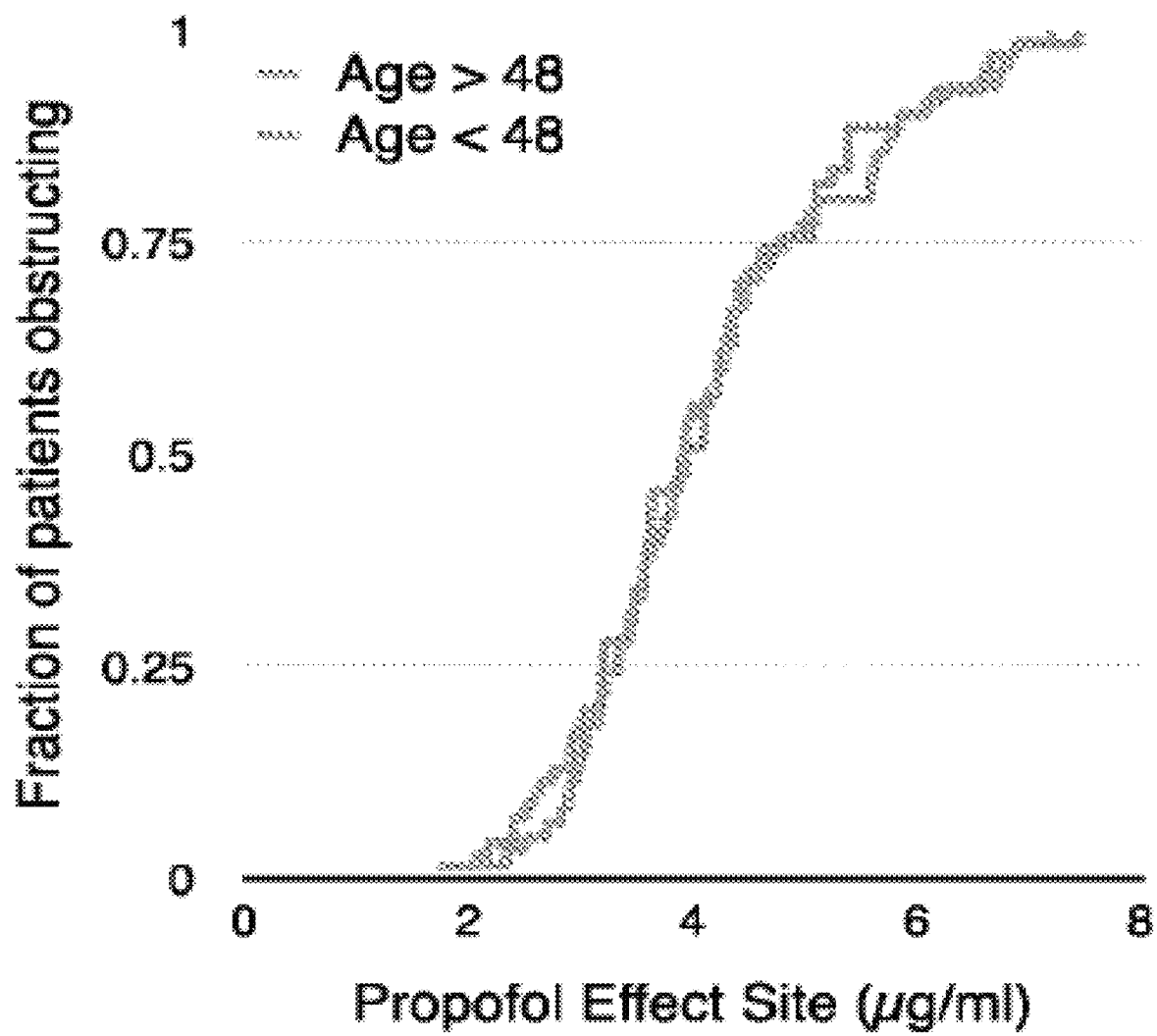
FIGS. 13A and 13B are exemplary graphs showing cumulative probability of airway collapse as determined for patients above and below the median age (48) (FIG. 13A) and above and below the median weight (100 kg) (FIG. 13B).
Figure 13B:
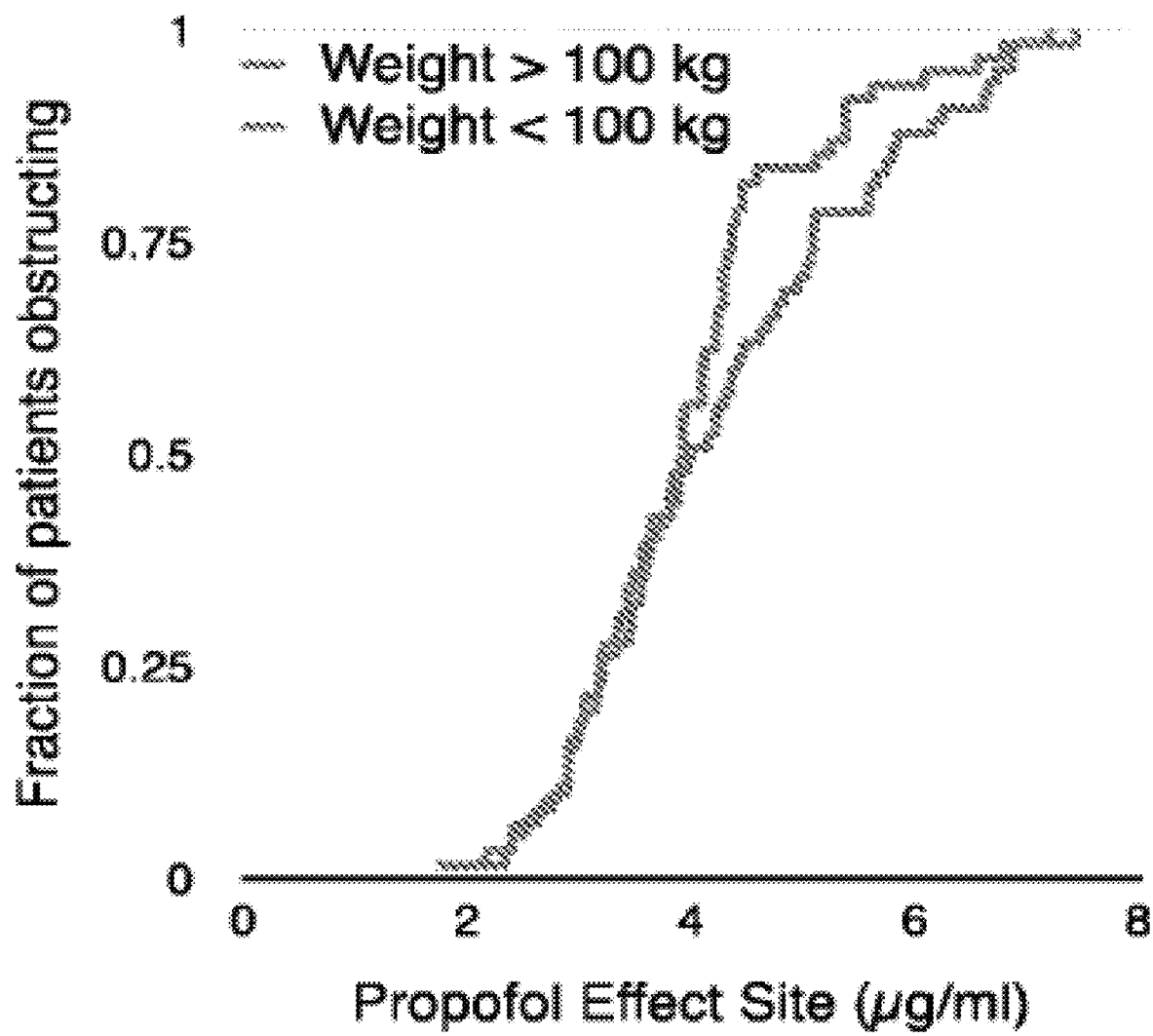

Data from 120 patients undergoing drug induced sleep endoscopy was utilized (Example 1 above). Propofol was administered using infusion sequences designed to produce a monotonic increase that would be similar for patients across a range of ages and weights. Effect site concentrations at the time of airway collapse were estimated, and the cumulative probability of airway collapse was determined for patients above and below the median age (48) and above and below the median weight (100 kg), as depicted in FIGS. 13A and 13B, respectively. Parameters of the pharmacokinetic model were adjusted by numerical methods to minimize the difference between each subgroup probability distribution and the distribution for the entire cohort. Given significantly larger cohorts, models tuned to finer gradations of age and weight could be obtained. A web-based system is demonstrated that provides a dosing schedule for DISE for a given age and weight and record of the time of airway collapse.

For most drugs, proper dosing is complicated by several factors. First, the time course of drug levels over time varies from patient to patient, i.e., pharmacokinetic uncertainty. Second, the drug level that corresponds to a desired clinical effect varies from patient to patient, i.e., pharmacodynamic uncertainty. Generally, clinicians "titrate to effect," but without insight into the pharmacokinetics, the dosing may result in peaks that occur too rapidly to accurately estimate the concentration at which the clinical effect occurred, or may take an inordinately long time to achieve the desired clinical effect.

While patient response to drug administration varies, this variability can be partitioned into that which can be predicted and that which cannot (at least at present). For example, on average, patients weighing 100 kg require more drug than patients weighing 50 kg. With enough 100 kg patients, the probability density function for achieving a clinical endpoint as a function of estimated drug level can be determined. If the only difference between 100 kg and 50 kg patients is pharmacokinetic, one would expect the probability density function for 100 kg patients to match that of 50 kg patients, so that an estimated drug level would yield the same probability of achieving the clinical endpoint irrespective of weight. By adjusting the parameters of the pharmacokinetic model, it is possible to do this. Given a large number of patients, it is now possible to create a large number of subcohorts and adjust the pharmacokinetic models for each so that the pharmacokinetic model is highly robust. To do this, many observations of patients making transitions to the clinical endpoint under similar administration sequences are required. Exemplary embodiments describe a system that addresses these issues.

Figure 14:
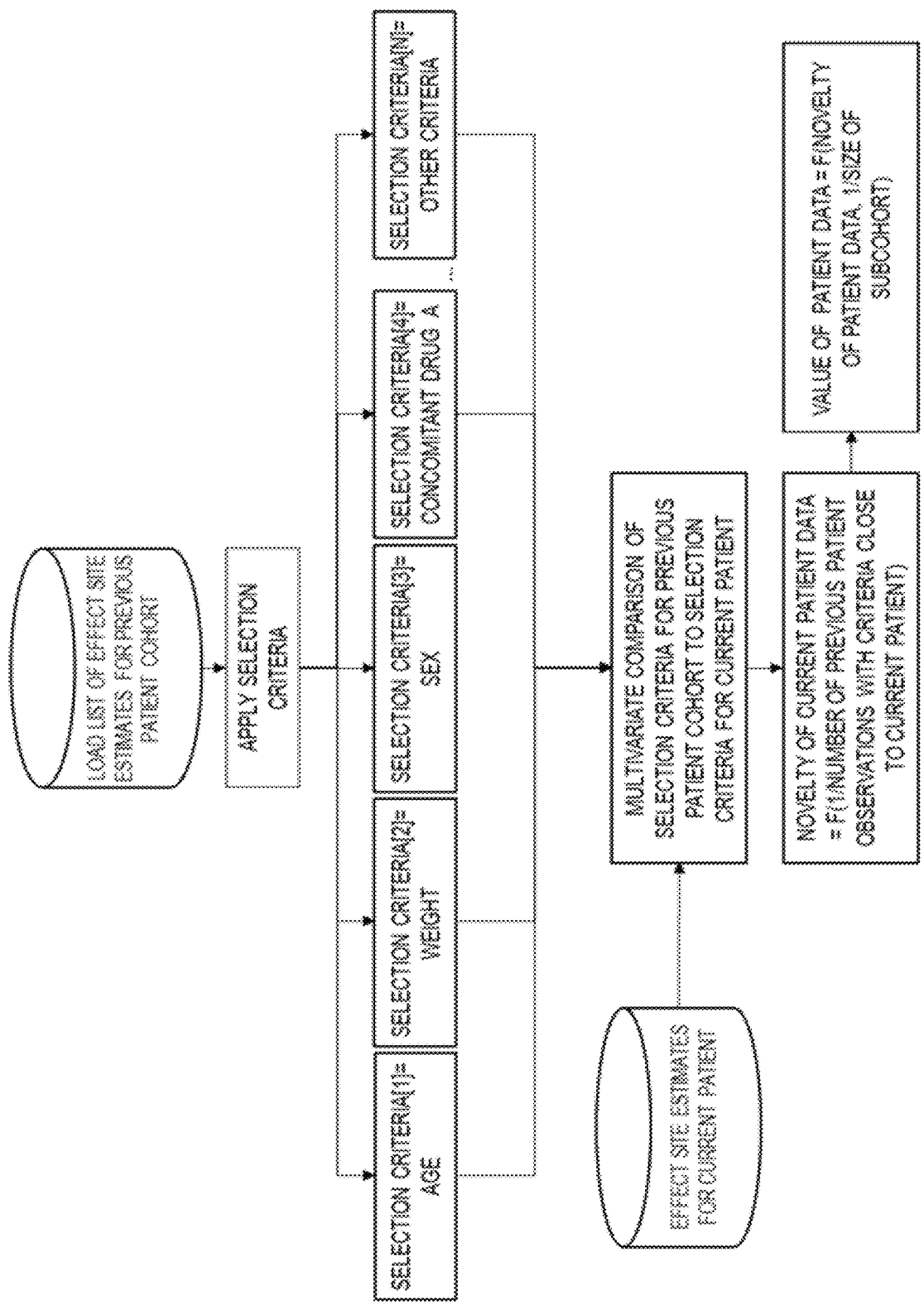
FIG. 14 is an exemplary flowchart illustrating an embodiment of implementing probability ramp control (PRC).

FIG. 14 illustrates an exemplary embodiment of implementing probability ramp control (PRC). In this embodiment, one or more selection criteria are applied to a list of observations and/or estimates of effect-site concentrations. The observations and/or estimates of effect-site concentrations may be taken from a cohort or subcohort of patients, for example a previous cohort or subcohort of patients observed during a transition to a desired clinical state. The selection criteria may be, for example, age, weight, sex, ethnicity, comorbidities, a concomitant drug, and/or other criteria. The selection criteria may be chosen to select a subset of patients who are similar in one or more aspects to a current patient. After the selection criteria have been applied to the list of observations and/or estimates of effect-site concentrations, a multivariate comparison of these observations and/or estimates, to observations and/or effect-site estimates for the current patient, may be performed. From this multivariate comparison, the novelty of the current patient data may be evaluated, and a value of the current patient data may be determined. The novelty is a measure of the fraction of previous observations and/or estimates that are in some sense close to the current patient. For example, a 99-year old patient may be considered to be novel if the next oldest patient were 85 years old.

Figure 15:
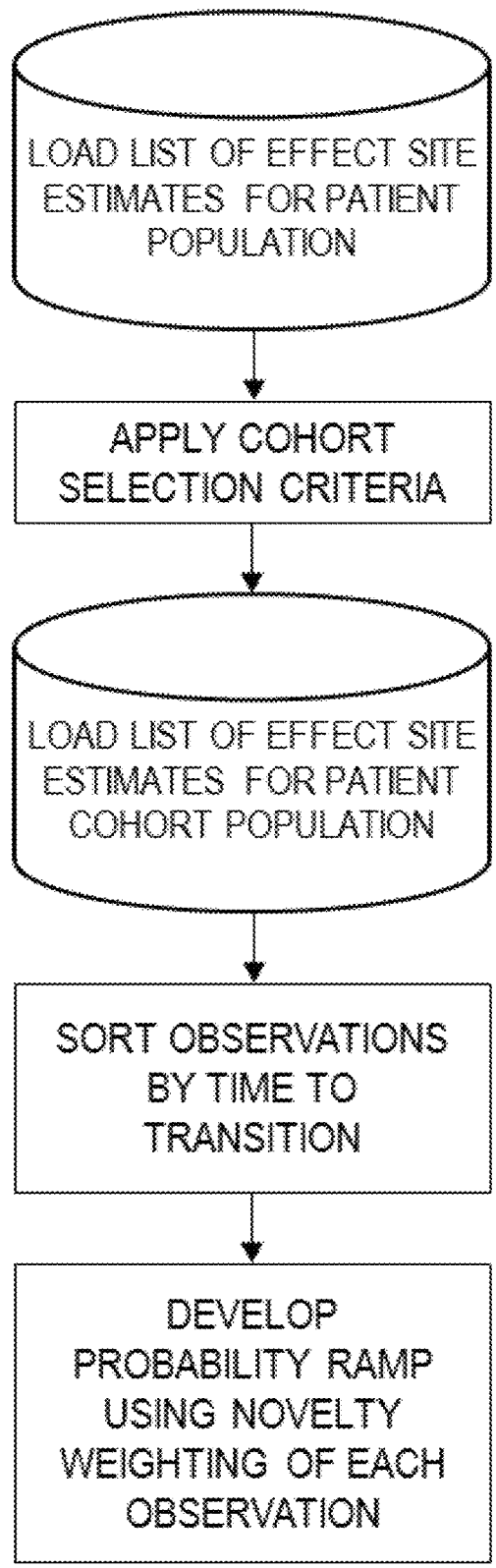
FIG. 15 is an exemplary flowchart illustrating another embodiment of implementing PRC.

FIG. 15 illustrates another exemplary embodiment of implementing PRC. In this embodiment, one or more selection criteria are applied to a list of observations and/or estimates of effect-site concentrations. The observations and/or estimates of effect-site concentrations may be taken from a cohort or subcohort of patients, for example a previous cohort or subcohort of patients observed during a transition to a desired clinical state. The selection criteria may be, for example, age, weight, sex, ethnicity, comorbidities, a concomitant drug, and/or other criteria. The selection criteria may be chosen to select a subset of patients who are similar in one or more aspects to a current patient. After the selection criteria have been applied to the list of observations and/or estimates of effect-site concentrations, a list may be arranged, ordered by the time to transition. This forms a trajectory of increasing effect-site concentration over time. For example, if there were 100 patients in a cohort, whose times to transition spanned a period of 100 seconds, then every second would yield a 1% increase in the fraction of the cohort that reached the transition to the desired clinical state. More generally, if there were N patients in a cohort, having times to transition spanning a period of M seconds, then every M/N seconds it would be expected for another patient in the cohort to make the transition to the desired clinical state. This uniform increase in probability is referred to as a probability ramp.

Figure 16:
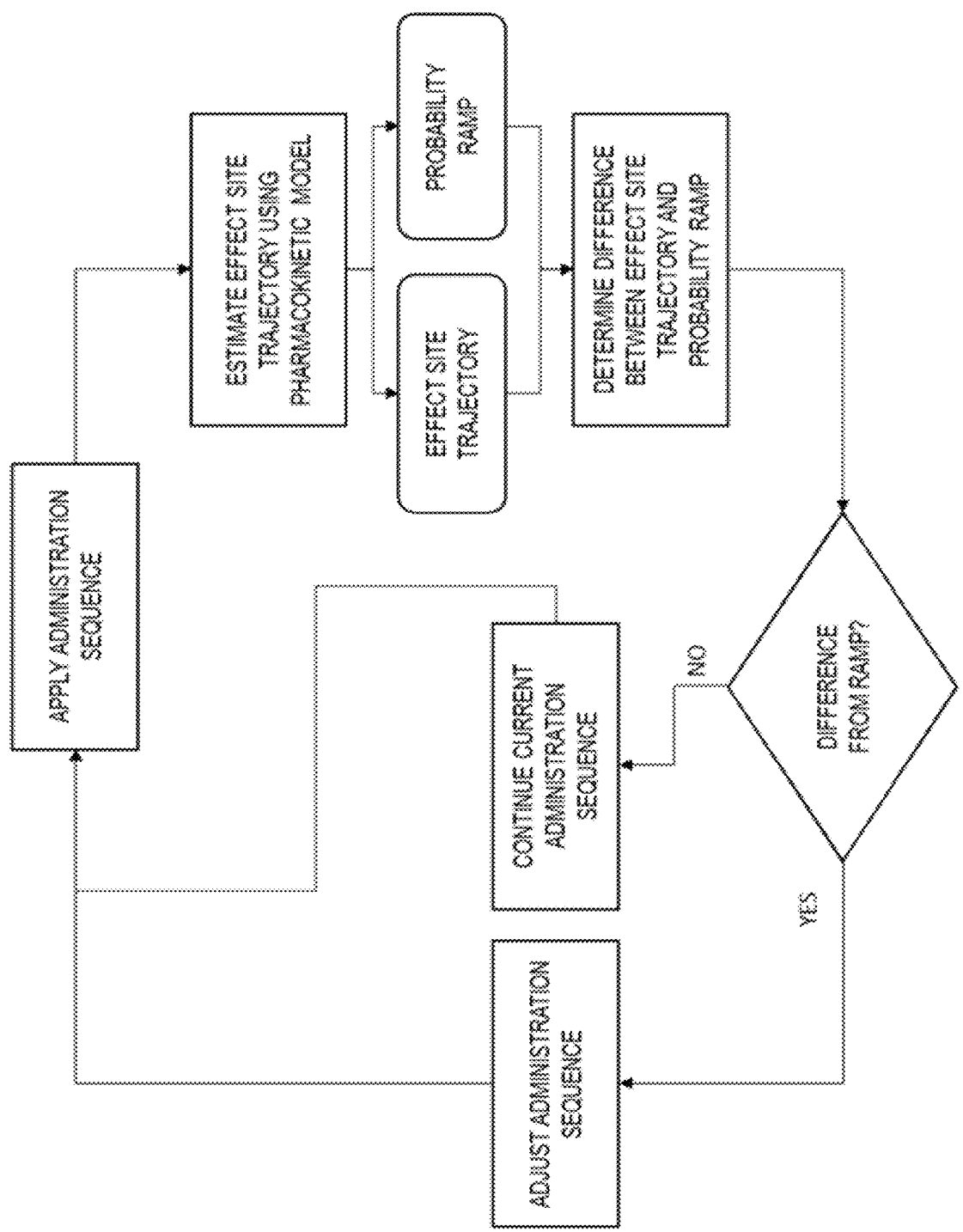
FIG. 16 is an exemplary flowchart illustrating an embodiment of using PRC in applying an administration sequence.

FIG. 16 illustrates an exemplary embodiment of using PRC in applying an administration sequence. In the case of an injectable drug, the administration sequence may begin with an initial loading bolus, an initial infusion, a secondary infusion, and a time at which a transition from the initial infusion to the secondary infusion occurs. In the case of an orally-administered drug, the administration sequence may reflect varied release rates of tablets and/or encapsulated pellets. The effect-site trajectory of the drug may be estimated using a pharmacokinetic model. The administration sequence may be selected to approximate a desired probability ramp in effect-site trajectory. A difference between the desired probability ramp and the effect-site trajectory may be determined, and the administration sequence may be adjusted iteratively based on this difference. If there is no difference between the desired probability ramp and the effect-site trajectory, or a minimal difference, then the current administration sequence may be maintained.

Figure 17:
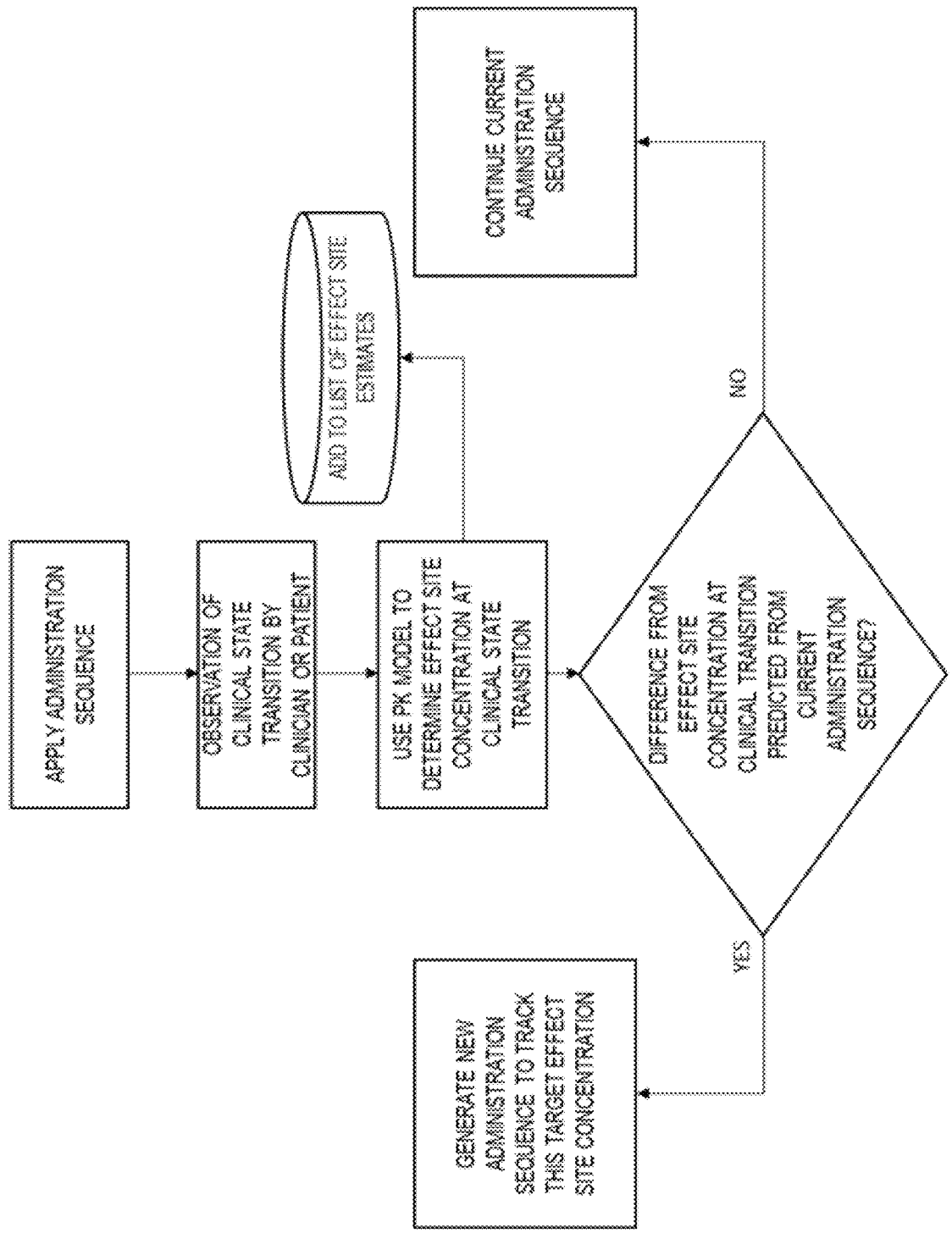
FIG. 17 is an exemplary flowchart illustrating an embodiment of determining an effect-site concentration for a clinical transition.

FIG. 17 illustrates an exemplary embodiment of determining an effect-site concentration for a clinical transition. In this embodiment, an administration sequence is applied, and a patient's transition to a clinical state is observed. A pharmacokinetic model then may be used to calculate the effect-site concentration at the time of the clinical transition. The calculated effect-site concentration may be used in two ways. First, it may be used to calculate a new or revised administration sequence that maintains the effect-site concentration at the desired target. Second, it may be added to a list of effect-site concentration measurements used to approximate a desired probability ramp in the future. If the effect-site concentration calculated from the pharmacokinetic model at the time of the clinical transition is different from the effect-site concentration predicted from the current administration sequence, then a new or revised administration sequence may be determined. Alternatively, if the effect-site concentration calculated from the pharmacokinetic model at the time of the clinical transition is the same as, or within an acceptable margin of error of, the effect-site concentration predicted from the current administration sequence, then the current administration sequence may be maintained.

Embodiments of the system may include a titration system that provides a dosing schedule for the drug that will cause the drug levels to proceed from the lowest level at which any patient ever responds, to the highest level ever required over a defined interval. The schedule may be designed so that the probability of achieving the clinical endpoint increases linearly over the interval; this is termed a probability ramp. The titration system may utilize a probability density function for the subcohort. The dosing schedule may be designed to require a minimum number of changes in administration rate, making it possible to implement by a clinician manually administering drugs, but the dosing schedule could also be transmitted directly to an infusion pump or other automated infusion system. An example of the dosing schedule is depicted in FIG. 4.

Embodiments of the system also may include an observation system that records the time of transition to the desired clinical state. The transition can be an observation by a clinician (e.g., loss of response to a stimulus), or a measurement from an automated monitor (e.g., processed EEG). The transition can alternatively be observed and reported by the patient. In exemplary embodiments, the patient may self-report a transition to an adequate state of anxiolysis. Exemplary embodiments include using objective measures to determine a desired clinical state, such as EEG, heart-rate variability, or other measurable parameters associated with the desired clinical state. The observation may also be of a side effect of the drug.

Embodiments of the system also may include an estimation system that estimates the drug level at the time of transition using the pharmacokinetic model.

Embodiments of the system also may include a maintenance system that provides a dosing schedule to maintain the drug level at the level identified by the estimation system. The inventor previously demonstrated herein that basing maintenance on an identified clinical endpoint decreases the error in maintaining this clinical endpoint in comparison to targeting an effect site estimate associated with the 50% probability of achieving the endpoint.

Embodiments of the system also may include a probability update system that incorporates the observation into a subcohort sharing the factors associated with drug variability and updates the pharmacokinetic model for that subcohort to minimize the difference between the probability density function for the subcohort and the entire cohort of patients. This probability density function then may be used in subsequent applications of the system.

Embodiments of the system also may include a value system that determines the extent to which an observation improves the overall system. Observations for patients belonging to subcohorts with few members may be more valuable than ones belonging to subcohorts with many members. Observations at the extremes of drug levels may be more valuable than observations near the median value. The value system also may consider the value of the information provided by the system. The intent of the value system could be to reward early adopters and users who care for patients at the extremes to ensure the system provides valuable information, while providing a revenue stream based on that value.

Clinicians using embodiments of the system may gain several advantages. First, the embodiments may provide a dosing schedule that has been demonstrated to avoid overshoot into airway collapse. The embodiments may be based on observations of clinicians in a large number of patients, but may adjust to subcohorts. The embodiments of the system may be utilized with preexisting infusion systems, and may use only a low bandwidth internet connection, making embodiments of the system useful in remote care settings.

Patients using embodiments of the system may benefit by detection of racial or familial associations of unusual responses to drugs.

The embodiments of the system provide advantages for society. Because the embodiments provide valuable information to users, it is likely that clinicians will use the embodiments, and in doing so, create a corpus of knowledge of drug sensitivity and side effects. The system embodiments may also be useful in quality assurance by recognizing providers who have outcomes significantly different from population norms. Finally, the system embodiments may permit new care models in which skilled clinicians can care for multiple patients simultaneously.

In the above description, an embodiment is an example or implementation. The various appearances of "one embodiment," "an embodiment" or "some embodiments" do not necessarily all refer to the same embodiments.

Although various features of the embodiments may be described in the context of a single embodiment, the features may also be provided separately or in any suitable combination. Conversely, although the embodiments may be described herein in the context of separate embodiments for clarity, the various embodiments may also be implemented in a single embodiment.

Reference in the specification to "some embodiments," "an embodiment," "one embodiment," or "other embodiments" means that a particular feature, structure, or characteristic described in connection with the embodiments is included in at least some embodiments, but not necessarily all embodiments.

It is to be understood that the phraseology and terminology employed herein is not to be construed as limiting and are for descriptive purpose only.

The principles and uses of the teachings of the embodiments may be better understood with reference to the accompanying description, figures and examples.

It is to be understood that the details set forth herein do not construe a limitation to an application of the embodiments.

Furthermore, it is to be understood that the embodiments can be carried out or practiced in various ways and that the embodiments can be implemented in embodiments other than the ones outlined in the description above.

It is to be understood that the terms "including," "comprising," "consisting," and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may," "might," "can," or "could" be included, that particular component, feature, structure, or characteristic is not required to be included.

Where applicable, although state diagrams, flow diagrams or both may be used to describe embodiments, the embodiments are not limited to those diagrams or to the corresponding descriptions. For example, flow need not move through each illustrated box or state, or in exactly the same order as illustrated and described.

Methods of the embodiments may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the embodiments belong.

The descriptions, examples, methods and materials presented in the claims and the specification are not to be construed as limiting but rather as illustrative only.

Meanings of technical and scientific terms used herein are to be commonly understood as by one of ordinary skill in the art to which the embodiments belong, unless otherwise defined.

The embodiments may be implemented in the testing or practice with methods and materials equivalent or similar to those described herein.

The disclosed embodiments should not be construed as limitations, but rather as exemplifications of some of the preferred embodiments. Other possible variations, modifications, and applications are also within the scope of the embodiments. Accordingly, the scope of the embodiments should not be limited by what has thus far been described, but by the appended claims and their legal equivalents.

I claim:

1. A method for dosing a drug to a patient comprising:
performing a first administering of the drug to the patient according to a titration dosing schedule obtained from a database, the titration dosing schedule being specific to a subcohort of a cohort of patients to which the patient is assigned and based on observations of previous patient responses to the drug, wherein
the patient is assigned to the subcohort of the cohort based at least on a match between one of race or ethnicity of the patient and the patients of the subcohort, and
the performing the first administering of the drug includes administration of the drug as a bolus and, subsequently, at an initial infusion rate that is constant;
monitoring the patient during the performing the first administering to determine when a desired clinical endpoint is reached, wherein the desired clinical endpoint is sedation, visible airway collapse, airway obstruction, or loss of genioglossus tone;
determining an effect-site concentration once the desired clinical endpoint is reached by estimating a drug level determined according to hybrid pharmacokinetic/pharmacodynamic modeling based on an amount of administered drug when the desired clinical endpoint was reached and a pharmacokinetic model for the subcohort;
formulating a maintenance dosing schedule at a secondary infusion rate to maintain the determined effect-site concentration, the secondary infusion rate being constant;
performing, responsive to determining the desired clinical endpoint is reached, a second administering of the drug to the patient, the second administering being performed according to the maintenance dosing schedule;
collecting patient data during the second administering and updating the subcohort to include the collected patient data;
updating the pharmacokinetic model for the subcohort using the collected patient data by minimizing a difference between a probability density function for the updated subcohort and the cohort; and
updating the titration dosing schedule to incorporate data from the monitoring of the patient, wherein
the drug is administered using a pump or other drug delivery device, and
the hybrid pharmacokinetic/pharmacodynamic modeling is without a physical connection to the pump or other drug delivery device associated with the first administering of the drug to the patient and the second administering of the drug to the patient.

2. The method of claim 1, wherein the drug is an anesthetic or sedative.

3. The method of claim 1, wherein the patient is further assigned to the subcohort of the cohort based at least on a match between one of age, weight, and gender of the patient and the patients of the subcohort.

4. The method of claim 1, wherein the titration dosing schedule comprises proceeding from a lowest level of the drug at which any previous patient ever responded as stored in the database, to a predetermined highest level of the drug ever required to reach the desired clinical endpoint, over a defined interval of time.

5. The method of claim 1, wherein the monitoring is performed by a clinician.

6. The method of claim 1, wherein the monitoring is performed using an automated monitor.

7. The method of claim 1, further comprising
using a user interface to record when the desired clinical endpoint is reached.

8. The method of claim 7, wherein the user interface is configured to
directly transmit the titration dosing scheduled and the maintenance dosing schedule to a controller configured to control administration of the drug during the first administering or the second administering.

9. The method of claim 7, wherein the database is stored on a server configured to communicate with the user interface via a network.

10. The method of claim 9, wherein the server is configured to be in further communication with additional user interfaces associated with other users.

11. The method of claim 1, further comprising a third administering of the drug to a new patient based on the updating the titration dosing schedule.

12. The method of claim 1, wherein the pump or other drug delivery device is configured to be manually controlled by a user.

13. The method of claim 1, wherein the pump or other drug delivery device is configured to be automatically controlled by a processor configured to receive the titration dosing schedule and the maintenance dosing schedule.

14. The method of claim 1, wherein the method is performed during a medical procedure on the patient.

15. A system for dosing a drug to a patient, comprising:
processing circuitry configured to:
perform a first administration of the drug to the patient according to a titration dosing schedule obtained from a database, the titration dosing schedule being specific to a subcohort of a cohort of patients to which the patient is assigned and based on observations of previous patient responses to the drug, wherein
the patient is assigned to the subcohort of the cohort based at least on a match between one of race or ethnicity of the patient and the patients of the subcohort, and
the first administration of the drug includes administration of the drug as a bolus and, subsequently, at an initial infusion rate that is constant, monitor the patient during the performing the first administration of the drug to determine when a desired clinical endpoint is reached, where in the desired clinical endpoint is sedation, visible airway collapse, airway obstruction, or loss genioglossus tissue, determine an effect-site concentration once the desired clinical endpoint is reached by estimating a drug level determined according to hybrid pharmacokinetic/pharmacodynamic modeling based on an amount of administered drug when the desired clinical endpoint was reached and a pharmacokinetic model for the subcohort, formulate a maintenance dosing schedule at a secondary infusion rate to maintain the determined effect-site concentration, the secondary infusion rate being constant, perform, responsive to the determination that the desired clinical endpoint is reached, a second administration of the drug to the patient, the second administration being performed according to the maintenance dosing schedule, collect patient data during the second administration and update the subcohort to include the collected patient data, update the pharmacokinetic model for the cohort using the collected patient data by minimizing a difference between a probability density function for the updated subcohort and the cohort, and update the titration dosing schedule to incorporate patient data from the monitoring, wherein the drug is administered using a pump or other drug delivery device, and the hybrid pharmacokinetic/pharmacodynamic modeling is without a physical connection to the pump or other drug delivery device associated with the first administering of the drug to the patient and the second administering of the drug to the patient.

16. A nontransitory computer-readable storage medium having computer executable instructions stored thereon, which when executed by a processor, causes the processor to perform a method for dosing a drug to a patient, comprising:

performing a first administering of the drug to the patient according to a titration dosing schedule obtained from a database, the titration dosing schedule being specific to a subcohort of a cohort of patients to which the patient is assigned and based on observations of previous patient responses to the drug, wherein the patient is assigned to the subcohort of the cohort based at least on a match between one of race or ethnicity of the patient and the patients of the subcohort, and the performing the first administering of the drug includes administration of the drug as a bolus and, subsequently, at an initial infusion rate that is constant;

monitoring the patient during the performing the first administering to determine when a desired clinical endpoint is reached, wherein the desired clinical endpoint is sedation, visible airway collapse, airway obstruction, or loss genioglossus tissue;

determining an effect-site concentration once the desired clinical endpoint is reached by estimating a drug level determined according to hybrid pharmacokinetic/pharmacodynamic modeling based on an amount of administered drug when the desired clinical endpoint was reached and a pharmacokinetic model for the subcohort;

formulating a maintenance dosing schedule at a secondary infusion rate to maintain the determined effect-site concentration, the secondary infusion rate being constant;

performing, responsive to determining the desired clinical endpoint is reached, a second administering of the drug to the patient, the second administering being performed according to the maintenance dosing schedule;

collecting patient data during the second administering and updating the subcohort to include the collected patient data;

updating the pharmacokinetic model for the subcohort using the collected patient data by minimizing a difference between a probability density function for the updated subcohort and the cohort; and updating the titration dosing schedule to incorporate data from the monitoring of the patient, wherein the drug is administered using a pump or other drug delivery device, and the hybrid pharmacokinetic/pharmacodynamic modeling is without a physical connection to the pump or other drug delivery device associated with the first administering of the drug to the patient and the second administering of the drug to the patient.

17. A method for determining a dosing of a drug to a new patient, comprising:

obtaining observations of at least one previous patient response to the drug generated by administering the drug to the at least one previous patient according to a titration dosing schedule obtained from a database, the titration dosing schedule being specific to a subcohort of a cohort of patients, wherein the at least one previous patient and the new patient are assigned to the subcohort based at least on, a match between one of age, weight, gender, race, or ethnicity of the patient and the at least one previous patient of the subcohort;

updating the titration dosing schedule to incorporate data from the observations of the at least one previous patient response to the drug, the updating including calculating, by processing circuitry, an update to the titration schedule for the new patient, performing a first administering of drug to the new patient according to the updated titration dosing schedule, wherein the performing the first administering of the drug includes administration of the drug as a bolus, and, subsequently, at an initial infusion rate;

monitoring the new patient during the performing of the first administering to determine when a desired clinical endpoint is reached, wherein the desired clinical endpoint is sedation, visible airway collapse, airway obstruction, or loss of genioglossus tissue;

determining an effect-site concentration once the desired clinical endpoint is reached by estimating a drug level determined according to hybrid pharmacokinetic/pharmacodynamic modeling based on an amount of administered drug when the desired clinical endpoint was reached and a pharmacokinetic model for the subcohort;

formulating a maintenance dosing schedule at a secondary infusion rate to maintain the determined effect-site concentration, the secondary infusion rate being constant;

performing, responsive to determining the desired clinical endpoint is reached, a second administering of the drug to the new patient, the second administering being performed according to the maintenance dosing schedule, wherein the drug is administered using a pump or other drug delivery device, and the hybrid pharmacokinetic/pharmacodynamic modeling is without a physical connection to the pump or other drug delivery device associated with the first administering of the drug to the patient and the second administering of the drug to the patient.

\* \* \* \* \*